United States Patent [19]
Wang

[11] Patent Number: 6,090,388
[45] Date of Patent: Jul. 18, 2000

[54] PEPTIDE COMPOSITION FOR PREVENTION AND TREATMENT OF HIV INFECTION AND IMMUNE DISORDERS

[75] Inventor: Chang Yi Wang, Cold Spring Harbor, N.Y.

[73] Assignee: United Biomedical Inc., Hauppauge, N.Y.

[21] Appl. No.: 09/100,409

[22] Filed: Jun. 20, 1998

[51] Int. Cl.$^7$ .......................... A61K 39/00; A61K 39/12; A61K 39/385; A61K 39/02; A61K 38/00

[52] U.S. Cl. .................... 424/185.1; 424/186.1; 424/189.1; 424/194.1; 424/236.1; 530/300; 530/323; 530/324; 530/326

[58] Field of Search .................... 530/300, 323, 530/326, 324; 424/189.1, 194.1, 185.1, 236.1, 186.1

[56] References Cited

U.S. PATENT DOCUMENTS

| | | | |
|---|---|---|---|
| 5,106,726 | 4/1992 | Wang | 435/5 |
| 5,759,551 | 6/1998 | Ladd | 424/198.1 |
| 5,843,446 | 6/1998 | Ladd | 424/184.1 |

FOREIGN PATENT DOCUMENTS

| | | |
|---|---|---|
| WO 94/25060 | 11/1994 | WIPO . |
| WO 95/11998 | 5/1995 | WIPO . |
| WO 97/46697 | 12/1997 | WIPO . |

OTHER PUBLICATIONS

C.Y. Wang, et al., *Science*, 254:285–288 (1991).
M. Loetscher, et al., *J. Bio. Chem.*, 269:232–237 (1994).
Dr. David Baltimore, *CNN Interactive*, (http://cnn.com/HEALTH/9802/01/aids.vaccine.search/index.html), Feb. 1, 1998.
M.C. Keefer, et al., *Aids Research And Human Retroviruses*, 10:1713 (1994).
R.B. Belshe, et al, *JAMA*, 272:475 (1994).
J.R. Mascola, et al., *The J. of Infectious Diseases*, 173:340–348 (1996).
C.V. Hanson, et al., *J. Clin. Microbiol.*, 28:2030–2034 (1990).
L.S.W. Sawyer, et al., *Journal of Virology*, 68:1342–1349 (1994).
T. Wrin, et al., *J. of Virology*, 69:39–48 (1995).
Y. Feng, et al. *Science*, 272:872–877 (1996).
B.J. Doranz, et al., *Cell*, 85:1149–1158 (1996).
B. Chackerian, et al., *J. of Virology*, 71:3932–3939 (1997).
O. Pleskoff, et al., *J. of Virology* 71:3259–3262 (1997).
Z. Chen, et al., *J. of Virology*, 71:2705–2714 (1997).
K.B. Cease, *Intern. Rev. Immunol.*, 7:85–107 (1990).
B.P. Babbitt, et al., *Nature*, 317:359–361 (1985).
M–P. Schutze, et al., *J. of Immunol.*, 135:2319–2322 (1985).
S.J. Brett, et al., *Eur. J. Immunol.*, 23:1608–1614 (1993).
G.E. Meister, et al., *Vaccine*, 13:581–591 (1995).
C. Ferrari, et al., *J. Clin. Invest.*, 88:214–222 (1991).
C.D. Partidos, et al., *J. of Gen. Virology*, 72:1293–1299 (1991).
A.J. Stagg, et al., *Immunology*, 79:1–9 (1993).
K.B. Cease, et al., *Proc. Natl. Acad. Sci, USA*, 84:4249–4253 (1987).
R.H. Meloen, et al., *Ann. Biol. Clin.*, 49:231–241 (1991).
A.M. Walfield, et al., *Aids Research Reviews*, 3:345–360 (1993).
G.A. Grant, ed., WH Freeman and Company: New York, 1992, pp. 63–67.

*Primary Examiner*—David Saunders
*Assistant Examiner*—Mary B. Tung
*Attorney, Agent, or Firm*—Morgan & Finnegan LLP

[57] ABSTRACT

The invention provides peptides comprising a sequence homologous to a portion of the CDR-2 like domain of CD4, covalently linked to a helper T cell epitope, and optionally to other immunostimulatory sequences as well. The invention provides for the use of such peptides as immunogens to elicit the production in mammals of high titer polyclonal auto-antibodies, which are specific to CD4 surface complex. These auto-antibodies prevent binding of HIV viral particles to CD4+ cells. The peptides are useful in pharmaceutical compositions, to provide an immunotherapy for HIV infection and to protect against HIV infection.

23 Claims, 1 Drawing Sheet

Deduced Amino Acid Sequence of Human CD4 (Sequence ID No.: 1)

```
         10         20         30         40         50         60         70
KKVVLGKKGD TVELTCTASQ KKSIQFHWKN SNQIKILGNQ GSFLTKGPSK LNDRADSRRS LWDQGNFPLI
         80         90        100        110        120        130        140
IKNLKIEDSD TYICEVEDQK EEVQLLVFGL TANSDTHLLQ GQSLTLTLES PPGSSPSVQC RSPRGKNIQG
        150        160        170        180        190        200        210
GKTLSVSQLE LQDSGTWTCT VLQNQKKVEF KIDIVVLAFQ KASSIVYKKE GEQVEFSFPL AFTVEKLTGS
        220        230        240        250        260        270        280
GELWWQAERA SSSKSWIIFD LKNKEVSVKR VTQDPKLQMG KKLPLHLTLP QALPQYAGSG NLTLALEAKT
        290        300        310        320        330        340        350
GKLHQEVNLV VMRATQLQKN LTCEVWGPTS PKLMLSLKLE NKEAKVSKRE KPVWVLNPEA GMWQCLLSDS
        360        370        380        390        400        410        420
SQVLLESNIK VLPTWSTPVQ PMALIVLGGV AGLLLFIGLG IFFCVRCRHR RRQAERMSQI KRLLSEKKTC
   430   433
QCPHRFQKTC SPI
```

|← Transmembrane Region →|    Cytoplasmic Tail

Fig. 1

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
       (A) LENGTH: 433 amino acids
       (B) TYPE: amino acid
       (D) TOPOLOGY: linear (ii) MOLECULE TYPE: peptide (xi) SEQUENCE DESCRIPTION: SEQ ID NO:1:

Lys Lys Val Val Leu Gly Lys Lys Gly Asp Thr Val
1               5                      10

Glu Leu Thr Cys Thr Ala Ser Gln Lys Lys Ser Ile
        15                  20

Gln Phe His Trp Lys Asn Ser Asn Gln Ile Lys Ile
25              30              35

Leu Gly Asn Gln Gly Ser Phe Leu Thr Lys Gly Pro
           40                  45

Ser Lys Leu Asn Asp Arg Ala Asp Ser Arg Arg Ser

-continued

```
                  50                  55                  60
Leu Trp Asp Gln Gly Asn Phe Pro Leu Ile Ile Lys
                     65                  70
Asn Leu Lys Ile Glu Asp Ser Asp Thr Tyr Ile Cys
             75                  80
Glu Val Glu Asp Gln Lys Glu Val Gln Leu Leu
 85                  90                  95
Val Phe Gly Leu Thr Ala Asn Ser Asp Thr His Leu
                100                 105
Leu Gln Gly Gln Ser Leu Thr Leu Thr Leu Glu Ser
    110                 115                 120
Pro Pro Gly Ser Ser Pro Ser Val Gln Cys Arg Ser
                125                 130
Pro Arg Gly Lys Asn Ile Gln Gly Gly Lys Thr Leu
        135                 140
Ser Val Ser Gln Leu Glu Leu Gln Asp Ser Gly Thr
145                 150                 155
Trp Thr Cys Thr Val Leu Gln Asn Gln Lys Lys Val
                160                 165
Glu Phe Lys Ile Asp Ile Val Val Leu Ala Phe Gln
    170                 175                 180
Lys Ala Ser Ser Ile Val Tyr Lys Lys Glu Gly Glu
                185                 190
Gln Val Glu Phe Ser Phe Pro Leu Ala Phe Thr Val
            195                 200
Glu Lys Leu Thr Gly Ser Gly Glu Leu Trp Trp Gln
205                 210                 215
Ala Glu Arg Ala Ser Ser Ser Lys Ser Trp Ile Ile
                220                 225
Phe Asp Leu Lys Asn Lys Glu Val Ser Val Lys Arg
    230                 235                 240
Val Thr Gln Asp Pro Lys Leu Gln Met Gly Lys Lys
                245                 250
Leu Pro Leu His Leu Thr Leu Pro Gln Ala Leu Pro
            255                 260
Gln Tyr Ala Gly Ser Gly Asn Leu Thr Leu Ala Leu
265                 270                 275
Glu Ala Lys Thr Gly Lys Leu His Gln Glu Val Asn
                280                 285
Leu Val Val Met Arg Ala Thr Gln Leu Gln Lys Asn
    290                 295                 300
Leu Thr Cys Glu Val Trp Gly Pro Thr Ser Pro Lys
                305                 310
Leu Met Leu Ser Leu Lys Leu Glu Asn Lys Glu Ala
            315                 320
Lys Val Ser Lys Arg Glu Lys Pro Val Trp Val Leu
325                 330                 335
Asn Pro Glu Ala Gly Met Trp Gln Cys Leu Leu Ser
                340                 345
Asp Ser Ser Gln Val Leu Leu Glu Ser Asn Ile Lys
    350                 355                 360
Val Leu Pro Thr Trp Ser Thr Pro Val Gln Pro Met
                365                 370
```

```
Ala Leu Ile Val Leu Gly Val Ala Gly Leu Leu
            375             380

Leu Phe Ile Gly Leu Gly Ile Phe Phe Cys Val Arg
385             390             395

Cys Arg His Arg Arg Arg Gln Ala Glu Arg Met Ser
            400             405

Gln Ile Lys Arg Leu Leu Ser Glu Lys Lys Thr Cys
    410             415             420

Gln Cys Pro His Arg Phe Gln Lys Thr Cys Ser Pro
                425             430

Ile
```

(2) INFORMATION FOR SEQ ID NO:2:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:2:

```
His Trp Lys Asn Trp Asn Gln Ile Lys Ile Leu Gly
1               5                   10

Asn Gln Gly Ser Phe Leu Thr Lys Gly Pro Ser Lys
            15              20

Leu Asn Asp Arg Ala Asp Ser Arg Arg Ser Leu Trp
25              30              35

Asp Gln Gly Asn
            40
```

(2) INFORMATION FOR SEQ ID NO:3:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:3:

```
Asn Gln Gly Ser Phe Leu Thr Lys Gly Pro Ser Lys
1               5                   10

Leu Asn Asp Arg Ala Asp Ser Arg Arg Ser Leu Trp
            15              20

Asp Gln Gly Asn
25
```

(2) INFORMATION FOR SEQ ID NO:4:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION: SEQ ID NO:4:

```
Cys His Trp Lys Asn Trp Asn Gln Ile Lys Ile Leu
1               5                   10

Gly Asn Gln Gly Ser Phe Leu Thr Lys Gly Pro Ser
```

```
                  15                  20
Lys Leu Asn Asp Arg Ala Asp Ser Arg Arg Ser Leu
 25                  30                  35

Trp Asp Gln Gly Asn Cys
             40
```

(2) INFORMATION FOR SEQ ID NO:5:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:5:

```
Cys Asn Gln Gly Ser Phe Leu Thr Lys Gly Pro Ser
 1               5                  10

Lys Leu Asn Asp Arg Ala Asp Ser Arg Arg Ser Leu
             15                  20

Trp Asp Gln Gly Asn Cys
 25                  30
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Ile, Met or Leu"

(ix) FEATURE:
        (A) NAME/KEY: Modified-site
        (B) LOCATION: 2
        (D) OTHER INFORMATION: /note= "Ser or Thr"

(ix) FEATURE:
        (A) NAME/KEY: Modified-site
        (B) LOCATION: 4
        (D) OTHER INFORMATION: /note= "Ile or Arg"

(ix) FEATURE:
        (A) NAME/KEY: Modified-site
        (B) LOCATION: 5
        (D) OTHER INFORMATION: /note= "Lys or Thr"

(ix) FEATURE:
        (A) NAME/KEY: Modified-site
        (B) LOCATION: 10
        (D) OTHER INFORMATION: /note= "His or Thr"

(ix) FEATURE:
        (A) NAME/KEY: Modified-site
        (B) LOCATION: 11
        (D) OTHER INFORMATION: /note= "Lys or Arg"

(ix) FEATURE:
        (A) NAME/KEY: Modified-site
        (B) LOCATION: 12
        (D) OTHER INFORMATION: /note= "Ile, Met or Leu"

(ix) FEATURE:
        (A) NAME/KEY: Modified-site
        (B) LOCATION: 14
        (D) OTHER INFORMATION: /note= "Gly or Thr"

```
        (ix) FEATURE:
              (A) NAME/KEY: Modified-site
              (B) LOCATION: 15
              (D) OTHER INFORMATION: /note= "Ile, Met or Val"

(xi) SEQUENCE DESCRIPTION: SEQ ID NO:6:

Xaa Xaa Glu Xaa Xaa Gly Val Ile Val Xaa Xaa Xaa
1               5                   10

Glu Xaa Xaa
        15

(2) INFORMATION FOR SEQ ID NO:7:

(i) SEQUENCE CHARACTERISTICS:
              (A) LENGTH: 16 amino acids
              (B) TYPE: amino acid
              (D) TOPOLOGY: linear (ii) MOLECULE TYPE: peptide (xi) SEQUENCE DESCRIPTION: SEQ ID NO:7:

Thr Ala Lys Ser Lys Lys Phe Pro Ser Tyr Thr Ala
1               5                   10

Thr Tyr Gln Phe
        15

(2) INFORMATION FOR SEQ ID NO:8:

(i) SEQUENCE CHARACTERISTICS:
              (A) LENGTH: 15 amino acids
              (B) TYPE: amino acid
              (D) TOPOLOGY: linear (ii) MOLECULE TYPE: peptide (xi) SEQUENCE DESCRIPTION: SEQ ID NO:8:

Phe Phe Leu Leu Thr Arg Ile Leu Thr Ile Pro Gln
1               5                   10

Ser Leu Asp
        15

(2) INFORMATION FOR SEQ ID NO:9:

(i) SEQUENCE CHARACTERISTICS:
              (A) LENGTH: 6 amino acids
              (B) TYPE: amino acid
              (D) TOPOLOGY: linear (ii) MOLECULE TYPE: peptide (xi) SEQUENCE DESCRIPTION: SEQ ID NO:9:

Pro Pro Xaa Pro Xaa Pro
1               5

(2) INFORMATION FOR SEQ ID NO:10:

(i) SEQUENCE CHARACTERISTICS:
              (A) LENGTH: 46 amino acids
              (B) TYPE: amino acid
              (D) TOPOLOGY: linear (ii) MOLECULE TYPE: peptide (xi) SEQUENCE DESCRIPTION: SEQ ID NO:10:

Cys His Trp Lys Asn Trp Asn Gln Ile Lys Ile Leu
1               5                   10
```

```
Gly Asn Gln Gly Ser Phe Leu Thr Lys Gly Pro Ser
        15                  20
Lys Leu Asn Asp Arg Ala Asp Ser Arg Arg Ser Leu
25                  30                  35
Trp Asp Gln Gly Asn Cys Pro Leu Ile Ile
            40                  45
```

(2) INFORMATION FOR SEQ ID NO:11:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:11:

```
Cys Asn Gln Gly Ser Phe Leu Thr Lys Gly Pro Ser
1               5                   10
Lys Leu Asn Asp Arg Ala Asp Ser Arg Arg Ser Leu
        15                  20
Trp Asp Gln Gly Asn Cys Pro Leu Ile Ile
25                  30
```

(2) INFORMATION FOR SEQ ID NO:12:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:12:

```
Lys Lys Lys Ile Ile Thr Ile Thr Arg Ile Ile Thr
1               5                   10
Ile Ile Thr Thr Ile Asp
        15
```

(2) INFORMATION FOR SEQ ID NO:13:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:13:

```
Thr Ile Asn Lys Pro Lys Gly Tyr Val Gly Lys Glu
1               5                   10
```

(2) INFORMATION FOR SEQ ID NO:14:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:14:

```
Phe Leu Thr Lys Gly Pro Ser Lys Leu Asn Asp Arg Ala
1               5                   10
```

(2) INFORMATION FOR SEQ ID NO:15:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:15:

Cys Gly Asn Gln Gly Ser Phe Leu Thr Lys Gly Cys
1               5                   10

(2) INFORMATION FOR SEQ ID NO:16:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:16:

Gly Pro Ser Lys Leu Asn Asp Arg Ala Asp Ser Arg
1               5                   10

Arg Ser Leu Trp Asp Gln
            15

(2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:17:

Asn Gln Gly Ser Phe Leu Thr
1               5

(2) INFORMATION FOR SEQ ID NO:18:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:18:

Cys Ile Leu Gly Asn Gln Gly Ser Phe Leu Thr Cys
1               5                   10

(2) INFORMATION FOR SEQ ID NO:19:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:19:

Asn Gln Gly Ser Phe Leu Thr Lys Gly Pro Ser Lys
1               5                   10

Leu Asn Asp Arg Ala Asp Ser Arg Arg Ser Leu Trp
            15                  20

Asp Gln Gly Asn Phe
25

(2) INFORMATION FOR SEQ ID NO:20:

(i) SEQUENCE CHARACTERISTICS:
        (A) LENGTH: 61 amino acids
        (B) TYPE: amino acid
        (D) TOPOLOGY: linear (ii) MOLECULE TYPE: peptide (xi) SEQUENCE DESCRIPTION: SEQ ID NO:20:

Ser Lys Leu Asn Asp Arg Ala Asp Ser Arg Arg Ser
1               5                   10

Leu Trp Asp Gln Gly Asn Phe Pro Leu Ile Ile Lys
        15                  20

Asn Leu Lys Ile Glu Asp Ser Asp Thr Tyr Ile Cys
25              30                  35

Glu Val Glu Asp Gln Lys Glu Glu Val Gln Leu Leu
            40              45

Val Phe Gly Leu Thr Ala Asn Ser Asp Thr His Leu
        50              55                  60

Leu (2) INFORMATION FOR SEQ ID NO:21:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:21:

Cys Ile Leu Gly Asn Gln Gly Ser Phe Leu Thr Lys
1               5                   10

Gly Cys (2) INFORMATION FOR SEQ ID NO:22:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:22:

Cys Ser Phe Leu Thr Lys Gly Pro Ser Lys Leu Asn
1               5                   10

Asp Arg Ala Asp Ser Arg Arg Cys
        15                  20

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:23:

```
Cys Leu Thr Lys Gly Pro Ser Lys Leu Asn Asp Arg
1               5                   10

Ala Asp Cys
        15

(2) INFORMATION FOR SEQ ID NO:24:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (xi) SEQUENCE DESCRIPTION: SEQ ID NO:24:

Cys Lys Gly Pro Ser Lys Leu Asn Asp Arg Ala Cys
1               5                   10

(2) INFORMATION FOR SEQ ID NO:25:

(i) SEQUENCE CHARACTERISTICS:
          (A) LENGTH: 20 amino acids
          (B) TYPE: amino acid
          (D) TOPOLOGY: linear (ii) MOLECULE TYPE: peptide (xi) SEQUENCE DESCRIPTION: SEQ ID NO:25:

Cys Ser Asp Thr Tyr Ile Cys Glu Val Glu Asp Gln
1               5                   10

Lys Glu Glu Val Gln Leu Leu Cys
        15                  20

(2) INFORMATION FOR SEQ ID NO:26:

(i) SEQUENCE CHARACTERISTICS:
          (A) LENGTH: 10 amino acids
          (B) TYPE: amino acid
          (D) TOPOLOGY: linear (ii) MOLECULE TYPE: peptide (xi) SEQUENCE DESCRIPTION: SEQ ID NO:26:

Cys Gly Asn Gln Gly Ser Phe Leu Thr Cys
1               5                   10

(2) INFORMATION FOR SEQ ID NO:27:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:27:

Cys Asn Gln Gly Ser Phe Leu Cys
1               5

(2) INFORMATION FOR SEQ ID NO:28:

(i) SEQUENCE CHARACTERISTICS:
          (A) LENGTH: 6 amino acids
          (B) TYPE: amino acid
          (D) TOPOLOGY: linear (ii) MOLECULE TYPE: peptide
```

(xi) SEQUENCE DESCRIPTION: SEQ ID NO:28:

Cys Gln Gly Ser Phe Cys
1               5

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:29:

Cys Asn Thr Arg Cys
1               5

(2) INFORMATION FOR SEQ ID NO:30:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:30:

Cys Leu Asn Thr Arg Ala Cys
1               5

(2) INFORMATION FOR SEQ ID NO:31:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:31:

Cys Pro Ser Lys Leu Asn Cys
1               5

(2) INFORMATION FOR SEQ ID NO:32:

(i) SEQUENCE CHARACTERISTICS:
        (A) LENGTH: 77 amino acids
        (B) TYPE: amino acid
        (D) TOPOLOGY: linear (ii) MOLECULE TYPE: peptide (xi) SEQUENCE DESCRIPTION: SEQ ID NO:32:

Thr Ala Lys Ser Lys Lys Phe Pro Ser Tyr Thr Ala
1               5                   10

Thr Tyr Gln Phe Gly Gly Phe Phe Leu Leu Thr Arg
            15                  20

Ile Leu Thr Ile Pro Gln Ser Leu Asp Gly Gly Cys
25                      30                  35

His Trp Lys Asn Trp Asn Gln Ile Lys Ile Leu Gly
                40                  45

Asn Gln Gly Ser Phe Leu Thr Lys Gly Pro Ser Lys
    50                  55                  60

Leu Asn Asp Arg Ala Asp Ser Arg Arg Ser Leu Trp

```
            65                  70
Asp Gln Gly Asn Cys
            75

(2) INFORMATION FOR SEQ ID NO:33:

(i) SEQUENCE CHARACTERISTICS:
        (A) LENGTH: 69 amino acids
        (B) TYPE: amino acid
        (D) TOPOLOGY: linear (ii) MOLECULE TYPE: peptide (xi) SEQUENCE DESCRIPTION: SEQ ID NO:33:

Thr Ala Lys Ser Lys Lys Phe Pro Ser Tyr Thr Ala
1               5                   10

Thr Tyr Gln Phe Gly Gly Phe Leu Leu Thr Arg
            15                  20

Ile Leu Thr Ile Pro Gln Ser Leu Asp Gly Gly Cys
25                  30                  35

Asn Gln Gly Ser Phe Leu Thr Lys Gly Pro Ser Lys
            40                  45

Leu Asn Asp Arg Ala Asp Ser Arg Arg Ser Leu Trp
50                  55                      60

Asp Gln Gly Asn Cys Pro Leu Ile Ile
            65

(2) INFORMATION FOR SEQ ID NO:34:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (xi) SEQUENCE DESCRIPTION: SEQ ID NO:34:

Thr Ala Lys Ser Lys Lys Phe Pro Ser Tyr Thr Ala
1               5                   10

Thr Tyr Gln Phe Gly Gly Phe Leu Leu Thr Arg
            15                  20

Ile Leu Thr Ile Pro Gln Ser Leu Asp Gly Gly Cys
25                  30                  35

His Trp Lys Asn Trp Asn Gln Ile Lys Ile Leu Gly
            40                  45

Asn Gln Gly Ser Phe Leu Thr Lys Gly Pro Ser Lys
50                  55                      60

Leu Asn Asp Arg Ala Asp Ser Arg Arg Ser Leu Trp
            65                  70

Asp Gln Gly Asn Cys Pro Leu Ile Ile
            75                  80

(2) INFORMATION FOR SEQ ID NO:35:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (xi) SEQUENCE DESCRIPTION: SEQ ID NO:35:
```

```
Thr Ala Lys Ser Lys Phe Pro Ser Tyr Thr Ala
1               5                   10

Thr Tyr Gln Phe Gly Gly Phe Phe Leu Leu Thr Arg
            15                  20

Ile Leu Thr Ile Pro Gln Ser Leu Asp Gly Gly Cys
25                  30                  35

Asn Gln Gly Ser Phe Leu Thr Lys Gly Pro Ser Lys
                40                  45

Leu Asn Asp Arg Ala Asp Ser Arg Arg Ser Leu Trp
    50                  55                  60

Asp Gln Gly Cys
            64

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Ser or Thr"

(ix) FEATURE:
        (A) NAME/KEY: Modified-site
        (B) LOCATION: 5
        (D) OTHER INFORMATION: /note= "Lys or Arg"

(ix) FEATURE:
        (A) NAME/KEY: Modified-site
        (B) LOCATION: 6
        (D) OTHER INFORMATION: /note= "Gly or Thr"

(ix) FEATURE:
        (A) NAME/KEY: Modified-site
        (B) LOCATION: 10
        (D) OTHER INFORMATION: /note= "His or Thr"

(ix) FEATURE:
        (A) NAME/KEY: Modified-site
        (B) LOCATION: 11
        (D) OTHER INFORMATION: /note= "Lys or Arg"

(ix) FEATURE:
        (A) NAME/KEY: Modified-site
        (B) LOCATION: 14
        (D) OTHER INFORMATION: /note= "Gly or Thr"

(xi) SEQUENCE DESCRIPTION: SEQ ID NO:36:

Ile Xaa Glu Ile Xaa Xaa Val Ile Val Xaa Xaa Ile
1               5                   10

Glu Xaa Ile
        15

(2) INFORMATION FOR SEQ ID NO:37:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (xi) SEQUENCE DESCRIPTION: SEQ ID NO:37:
```

```
Lys Lys Lys Ile Ile Thr Ile Thr Arg Ile Ile Thr
1               5                   10

Ile Ile Thr Thr Ile Asp Gly Gly Cys Asn Gln Gly
            15              20

Ser Phe Leu Thr Lys Gly Pro Ser Lys Leu Asn Asp
25                  30                  35

Arg Ala Asp Ser Arg Ser Leu Trp Asp Gln Gly
                40              45

Asn Cys
    50
```

(2) INFORMATION FOR SEQ ID NO:38:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:38:

```
Leu Ser Glu Ile Lys Gly Val Ile Val His Arg Leu
1               5                   10

Glu Gly Val
        15
```

(2) INFORMATION FOR SEQ ID NO:39:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:39:

```
Gly Ile Leu Glu Ser Arg Gly Ile Lys Ala Arg Ile
1               5                   10

Thr His Val Asp Thr Glu Ser Tyr
        15              20
```

(2) INFORMATION FOR SEQ ID NO:40:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:40:

```
Lys Lys Gln Tyr Ile Lys Ala Asn Ser Lys Phe Ile
1               5                   10

Gly Ile Thr Glu Leu
        15
```

(2) INFORMATION FOR SEQ ID NO:41:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:41:

Lys Lys Phe Asn Asn Phe Thr Val Ser Phe Trp Leu
1               5                   10

Arg Val Pro Lys Val Ser Ala Ser His Leu
            15                  20

(2) INFORMATION FOR SEQ ID NO:42:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:42:

Lys Lys Leu Arg Arg Leu Leu Tyr Met Ile Tyr Met
1               5                   10

Ser Gly Leu Ala Val Arg Val His Val Ser Lys Glu
            15                  20

Glu Gln Tyr Tyr Asp Tyr
25                  30

(2) INFORMATION FOR SEQ ID NO:43:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:43:

Tyr Asp Pro Asn Tyr Leu Arg Thr Asp Ser Asp Lys
1               5                   10

Asp Arg Phe Leu Gln Thr Met Val Lys Leu Phe Asn
            15                  20

Arg Ile Lys
25

(2) INFORMATION FOR SEQ ID NO:44:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:44:

Gly Ala Tyr Ala Arg Cys Pro Asn Gly Thr Arg Ala
1               5                   10

Leu Thr Val Ala Glu Leu Arg Gly Asn Ala Glu Leu
            15                  20

(2) INFORMATION FOR SEQ ID NO:45:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:45:

```
Val Ser Phe Gly Val Trp Ile Arg Thr Pro Pro Ala
1               5                   10

Tyr Arg Pro Pro Asn Ala Pro Ile Leu
            15              20
```

(2) INFORMATION FOR SEQ ID NO:46:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:46:

```
Ser Asp Phe Phe Pro Ser Val Arg Asp Leu Leu Asp
1               5                   10

Thr Ala Ser Ala Leu Tyr Arg Glu
            15              20
```

(2) INFORMATION FOR SEQ ID NO:47:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:47:

```
Pro His His Thr Ala Leu Arg Gln Ala Ile Leu Cys
1               5                   10

Trp Gly Glu Leu Met Thr Leu Ala
            15              20
```

(2) INFORMATION FOR SEQ ID NO:48:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:48:

```
Trp Val Arg Asp Ile Ile Asp Asp Phe Thr Asn Glu
1               5                   10

Ser Ser Gln Lys Thr
            15
```

(2) INFORMATION FOR SEQ ID NO:49:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:49:

```
Arg Ala Gly Arg Ala Ile Leu His Ile Pro Thr Arg
1               5                   10

Ile Arg Gln Gly Leu Glu Arg
            15
```

(2) INFORMATION FOR SEQ ID NO:50:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:50:

```
Ala Val Ala Glu Gly Thr Asp Arg Val Ile Glu Val
1               5                   10

Leu Gln Arg Ala Gly Arg Ala Ile Leu
        15                  20
```

(2) INFORMATION FOR SEQ ID NO:51:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:51:

```
Ala Leu Asn Ile Trp Asp Arg Phe Asp Val Phe Ser
1               5                   10

Thr Leu Gly Ala Thr Ser Gly Tyr Leu Lys Gly Asn
        15                  20

Ser
25
```

(2) INFORMATION FOR SEQ ID NO:52:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:52:

```
Asp Ser Glu Thr Ala Asp Asn Leu Glu Lys Thr Val
1               5                   10

Ala Ala Leu Ser Ile Leu Pro Gly His Gly
        15                  20
```

(2) INFORMATION FOR SEQ ID NO:53:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (xi) SEQUENCE DESCRIPTION: SEQ ID NO:53:

```
Glu Glu Ile Val Ala Gln Ser Ile Ala Leu Ser Ser
1               5                   10

Leu Met Val Ala Gln Ala Ile Pro Leu Val Gly Glu
        15                  20

Leu Val Asp Ile Gly Phe Ala Ala Thr Asn Phe Val
25              30                  35

Glu Ser Cys
```

(2) INFORMATION FOR SEQ ID NO:54:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:54:

Asp Ile Glu Lys Lys Ile Ala Lys Met Glu Lys Ala
1               5                   10

Ser Ser Val Phe Asn Val Val Asn Ser
        15                  20

(2) INFORMATION FOR SEQ ID NO:55:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:55:

Lys Trp Phe Lys Thr Asn Ala Pro Asn Gly Val Asp
1               5                   10

Glu Lys Ile Arg Ile
        15

(2) INFORMATION FOR SEQ ID NO:56:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:56:

Gly Leu Gln Gly Lys Ile Ala Asp Ala Val Lys Ala
1               5                   10

Lys Gly (2) INFORMATION FOR SEQ ID NO:57:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:57:

Gly Leu Ala Ala Gly Leu Val Gly Met Ala Ala Asp
1               5                   10

Ala Met Val Glu Asp Val Asn
        15

(2) INFORMATION FOR SEQ ID NO:58:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:58:

Ser Thr Glu Thr Gly Asn Gln His His Tyr Gln Thr
1               5                   10

Arg Val Val Ser Asn Ala Asn Lys
        15                  20

(2) INFORMATION FOR SEQ ID NO:59:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /note= "Ile, Met or Leu"

(ix) FEATURE:
            (A) NAME/KEY: Modified-site
            (B) LOCATION: 4
            (D) OTHER INFORMATION: /note= "Ser or Thr"

(ix) FEATURE:
            (A) NAME/KEY: Modified-site
            (B) LOCATION: 7
            (D) OTHER INFORMATION: /note= "Lys or Arg"

(ix) FEATURE:
            (A) NAME/KEY: Modified-site
            (B) LOCATION: 8
            (D) OTHER INFORMATION: /note= "Gly or Thr"

(ix) FEATURE:
            (A) NAME/KEY: Modified-site
            (B) LOCATION: 12
            (D) OTHER INFORMATION: /note= "His or Thr"

(ix) FEATURE:
            (A) NAME/KEY: Modified-site
            (B) LOCATION: 13
            (D) OTHER INFORMATION: /note= "Lys or Arg"

(ix) FEATURE:
            (A) NAME/KEY: Modified-site
            (B) LOCATION: 14
            (D) OTHER INFORMATION: /note= "Ile, Met or Leu"

(ix) FEATURE:
            (A) NAME/KEY: Modified-site
            (B) LOCATION: 16
            (D) OTHER INFORMATION: /note= "Gly or Thr"

(ix) FEATURE:
            (A) NAME/KEY: Modified-site
            (B) LOCATION: 17
            (D) OTHER INFORMATION: /note= "Ile, Met or Val"

(xi) SEQUENCE DESCRIPTION: SEQ ID NO:59:

Ile Ser Xaa Xaa Glu Ile Xaa Xaa Val Ile Val Xaa
1               5                   10

Xaa Xaa Glu Xaa Xaa Leu Phe
        15

(2) INFORMATION FOR SEQ ID NO:60:

(i) SEQUENCE CHARACTERISTICS:
            (A) LENGTH: 47 amino acids

```
          (B) TYPE: amino acid
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /note= "Ile, Met or Leu"

(ix) FEATURE:
          (A) NAME/KEY: Modified-site
          (B) LOCATION: 2
          (D) OTHER INFORMATION: /note= "Ser or Thr"

(ix) FEATURE:
          (A) NAME/KEY: Modified-site
          (B) LOCATION: 4
          (D) OTHER INFORMATION: /note= "Ile or Arg"

(ix) FEATURE:
          (A) NAME/KEY: Modified-site
          (B) LOCATION: 5
          (D) OTHER INFORMATION: /note= "Lys or Thr"

(ix) FEATURE:
          (A) NAME/KEY: Modified-site
          (B) LOCATION: 10
          (D) OTHER INFORMATION: /note= "His or Thr"

(ix) FEATURE:
          (A) NAME/KEY: Modified-site
          (B) LOCATION: 11
          (D) OTHER INFORMATION: /note= "Lys or Arg"

(ix) FEATURE:
          (A) NAME/KEY: Modified-site
          (B) LOCATION: 12
          (D) OTHER INFORMATION: /note= "Ile, Met or Leu"

(ix) FEATURE:
          (A) NAME/KEY: Modified-site
          (B) LOCATION: 14
          (D) OTHER INFORMATION: /note= "Gly or Thr"

(ix) FEATURE:
          (A) NAME/KEY: Modified-site
          (B) LOCATION: 15
          (D) OTHER INFORMATION: /note= "Ile, Met or Val"

(xi) SEQUENCE DESCRIPTION: SEQ ID NO:60:

Xaa Xaa Glu Xaa Xaa Gly Val Ile Val Xaa Xaa Xaa
1               5                   10

Glu Xaa Xaa Gly Gly Cys Asn Gln Gly Ser Phe Leu
            15                  20

Thr Lys Gly Pro Ser Lys Leu Asn Asp Arg Ala Asp
25                      30                  35

Ser Arg Arg Ser Leu Trp Asp Gln Gly Asn Cys
                40                  45

(2) INFORMATION FOR SEQ ID NO:61:

(i) SEQUENCE CHARACTERISTICS:
          (A) LENGTH: 16 amino acids
          (B) TYPE: amino acid
          (D) TOPOLOGY: linear (ii) MOLECULE TYPE: peptide (xi) SEQUENCE DESCRIPTION: SEQ ID NO:61:

Asp Leu Ser Asp Leu Lys Gly Leu Leu Leu His Lys
1               5                   10
```

```
(2) INFORMATION FOR SEQ ID NO:62:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:62:

Glu Ile Ser Glu Ile Arg Gly Ile Ile Ile His Arg
1               5                   10
Ile Glu Gly Ile
        15

(2) INFORMATION FOR SEQ ID NO:63:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:63:

Asp Val Ser Asp Val Lys Gly Val Val Val His Lys
1               5                   10
Val Asp Gly Val
        15

(2) INFORMATION FOR SEQ ID NO:64:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:64:

Asp Phe Ser Asp Phe Lys Gly Phe Phe Phe His Lys
1               5                   10
Phe Asp Gly Phe
        15
```

PEPTIDE COMPOSITION FOR PREVENTION AND TREATMENT OF HIV INFECTION AND IMMUNE DISORDERS

FIELD OF THE INVENTION

This invention is directed to the use of a peptide composition as an immunogen, with each peptide contained therein comprising a target antigenic site that is recognized by antibodies against a host cell receptor/coreceptor complex for HIV. Said complex is comprised of CD4 associated with a chemokine receptor domain. The target antigenic site is produced in a cyclic form covalently linked to (1) a carrier protein through chemical coupling, or preferably to (2) a peptide helper T cell epitope and other immunostimulatory peptide sequences in a linear tandem form, produced by chemical coupling or more preferably by direct synthesis. More particularly, the present invention relates to the use of such peptide composition as an immunogen to elicit the production in healthy mammals including humans, of high titer antibodies which have broad neutralizing activities against primary isolates from all clades of HIV type 1 (HIV-1) and primary isolates of HIV type 2 (HIV-2). The present invention is also directed to a method of using said peptide composition as an immunogen for prevention and treatment of immunodeficiency virus infection as well as for treatment of undesirable immune responses such as transplant rejection, and autoimmune disorders such as rheumatoid arthritis, systemic lupus erythematosis, and psoriasis.

BACKGROUND OF THE INVENTION

Notwithstanding intensive research for a vaccine in the 14 years since the discovery and characterization of HIV, major obstacles remain for HIV vaccine and immunotherapy development. These hurdles include HIV-1 variability, a lack of understanding of the virus structure, and a lack of understanding of the immune responses necessary for prevention of HIV infection. See D. Burton and J. Moore, Nature Medicine, 1998, 4:495–48. The head of the US government's AIDS vaccine research committee stated on Feb. 1, 1998 that a safe vaccine to prevent AIDS could still be more than a decade away from testing, because too much remains unknown about how the body's immune system works (http://cnn.cm/HEALTH/9802/01/aids.vaccine.search).

There was early optimism for efficacious recombinant HIV-1 envelope subunit vaccines (e.g., gp120 and gp160 vaccine products) given that vaccinee sera from several clinical trials were capable of neutralizing laboratory isolates of HIV-1 in vitro (Belshe et al., *J. Am. Med. Assoc.*, 1994, 272:475; Keefer et al., *AIDS Res. Hum Retroviruses*, 1994, 10:1713). This optimism was shaken when the vaccinee sera were found to be largely ineffective in neutralizing HIV-1 primary patient isolates (Hanson, *AIDS Res. Hum Retroviruses*, 1994, 10:645; Mascola et al., *J Infect Dis.*, 1996, 173:340). These disappointing findings led NIH to decide in June 1994 to postpone costly large-scale efficacy trials of several recombinant envelope protein based HIV subunit vaccines.

HIV vaccine research now focuses on primary isolates which are believed to more closely resemble HIV strains responsible for human infection than do the commonly used laboratory strains (Sawyer et al., *J Virol*, 1994, 68:1342; Wrin et al., *J Virol*, 1995, 69:39). Primary isolates of HIV-1 are obtained by limited cultivation of patient PBMCs or plasma with uninfected PBMCs. Primary viruses can be readily distinguished by phenotype as discussed below from the T cell line adapted (TCLA) viruses such as IIb/LAI, SF2, and MN, which have been passaged over time in human T-lymphoid cell lines and have become well-adapted to grow in these T cell lines:

(1) Unlike TCLA viruses, most primary isolates do not readily grow in T cell lines.

(2) Unlike TCLA viruses which are all syncytium-inducing, primary isolates include both syncytium-inducing (SI) isolates that induce syncytium formation in PBMC culture and non-syncytium-inducing (NSI) isolates. Among the SI primary isolates, most will replicate in the especially HIV-sensitive T cell line MT2, but few can replicate in the less permissive T cell lines such as CEM or H9 that are commonly used for the culture of TCLA isolates. Non-syncytium-inducing (NSI) primary isolates replicate only in primary T cells.

(3) Primary isolates are highly resistant to in vitro neutralization by recombinant soluble forms of the viral receptor protein CD4 (rsCD4) requiring 200–2700 times more rsCD4 than TCLA strains for comparable neutralization (Daar et al., *PNAS USA*, 1990, 87:6574–6578).

(4) Primary isolates are also resistant to neutralizing antibodies elicited by the use of gp120 (envelope) vaccines. In contrast, The TCLA strains are sensitive to neutralization by antibodies with specificities for the viral envelope (Sawyer et al., *J Virol*, 1994, 68:1342; and, Mascola et al., 1996).

These phenotypic characteristics of primary isolates are due to poorly understood structural features of HIV, particularly the inaccessible quality of the viral envelope with respect to anti-env antibodies (D. Burton and J. Moore, *Nature Medicine*, 1998, 4:495–498). Viral variability, a genotypic characteristic, also remains as an obstacle to the development of HIV vaccines of worldwide efficacy (Mascola et al., 1996). These factors together account for the unexpected failure of virally-directed AIDS vaccines which were developed against readily grown TCLA homotypic strains. An alternative approach to HIV vaccine development could be by intervention on the HIV receptors of the host cell, thereby blocking infection by preventing HIV from binding to or fusing with susceptible cells. The cell-directed approach offers methods to overcome the hypervariability of the HIV envelope and phenotypic diversity.

A cell-directed approach for protection from HIV infection was suggested by active and passive immunization studies in the SIV rhesus macaque model which showed that anti-cell antibodies greatly contributed to protection from infection (Stott, *Nature*, 1991, 353:393). In addition, monoclonal antibodies directed against CD4, a T cell receptor for MHC Class II molecules and the primary receptor for HIV binding, have long been known to block infection in HIV-1 neutralization assays in a manner that is dependent on the CD4 epitope, not the virus strain (Sattentau et al., *Science*, 1986; 234:1120). Of particular relevance for a cell-directed approach to immunoprophylaxis, anti-CD4 monoclonal antibodies have been effective in blocking infection of cells by primary isolates (Daar et al., *Proc. Natl. Acad. Sci. USA*, 1990; 87: 6574; and Hasunuma et al., *J Immunol.*, 1992; 148:1841). Other potentially effective cell-directed approaches can be to target chemokine receptors CXCR4, CCR5, CCR2b, and CCR3 that recently have been identified as coreceptors for HIV (Feng et al., *Science*, 1996; 272:872; and, Doranz et al., Cell, 1996; 85:1149). These coreceptors function together with CD4 to initiate post-binding interactions of the viral envelope glycoprotein with the host cell membrane and in post-entry steps of retrovirus replication (Chackerian et al., *J Virol*, 1997; 71:3932). The requirement for both CD4 and a coreceptor for efficient HIV binding and fusion suggests that either or both of these molecules may be good targets for cell-directed strategies to inhibit infection. Antibodies directed to a host cell CD4/coreceptor complex have been shown to affect both binding and post-binding steps of HIV infection (Wang, WO 97/46697). These antibodies neutralized virus-to-cell or cell-to-cell transmission of both syncytium-inducing (SI) and non-SI (NSI) strains of HIV. A chemokine antagonist that binds to CCR5 has also been shown to be effective in preventing infection by both SI and NSI viruses (Simmons et al., *Science*, 1997; 276:276). Neutralization of NSI isolates is particularly significant as NSI strains are believed to be responsible for most HIV transmission and are frequently resistant to anti-HIV antibodies which neutralize TCLA isolates (Fauci, 1996). The agents that target the cellular receptors of HIV avoid the need to confront diverse phenotypes and the hypervariability of the viral envelope, and in addition offer potential neutralization activity against HIV-2 and SIV (Chen et al, *J Virol*, 1997; 71:2705; Pleskoff et al., *J Virol*, 1997; 71:3259; WO 97/46697).

A host cell receptor/coreceptor complex comprising CD4 and a chemokine coreceptor on the surface of the host T cells, which facilitates viral binding and entry into the host T cells, is reported to be an effective target for neutralizing antibodies in a co-pending patent application (U.S. Ser. No. 08/657,149 also published as WO 97/46697). In that application, the present inventor demonstrated that except for antibodies directed against this cell surface antigen complex, no other anti-cell antibodies raised in response to cell surface antigens on HPB-ALL cells neutralized HIV-1 primary isolates. Antibodies with the desired properties as described in that application can block infection of monkeys by SIV, in vivo HIV-1 infection of the human immune system reconstituted in mice, in vitro infections of human cells by HIV-1 primary isolates of diverse phenotypes and genotypes and block infection of human cells by HIV-2. This cell surface antigen complex comprising the CD4 receptor associated with a chemokine coreceptor (CD4/coreceptor complex) acts as a target for protective anti-cell antibodies.

Anti-cell antibodies to the CD4/coreceptor complex display a more effective pattern of neutralization against relevant HIV strains than do anti-virus antibodies directed against the viral envelope. As shown in the co-pending application (WO 97/46697), a monoclonal antibody (MAb B4), produced against HPB-ALL and having a moderate reactivity against the recombinant soluble CD4 (rsCD4) protein and a strong binding to the HPB-ALL cells, i.e., with specificity for the CD4/coreceptor cell surface complex, was found highly effective in neutralizing primary isolates of HIV-1 but less effective in neutralizing TCLA strains. In contrast, anti-env antibodies display the reverse pattern for preferential neutralization of TCLA strains.

It was found that MAb B4 neutralized HIV primary isolates in an in vitro microplaque assay at a concentration of <10 μg/ml. In contrast, polyclonal antibodies with high titer (>5 $Log_{10}$) specificity for recombinant soluble CD4 (rsCD4) failed to display any neutralizing activity for HIV primary isolates despite their strong T cell binding activities. Thus, the primary isolates appear to be preferentially sensitive to the antibody with specificity for the cell surface CD4/coreceptor antigen complex, in comparison to antibodies with a pure CD4 specificity. The extensive characterization of HIV neutralization by anti-CD4/coreceptor complex antibodies includes MAb B4 and its homologs MAb M2 and MAb B13 (WO 97/46697).

The mechanism for the broad neutralizing activity of antibodies to the CD4/coreceptor complex is unclear because of the diverse roles of that cell surface complex in mediating HIV infection, as shown by the ability of those antibodies to affect both binding and post-binding steps of HIV infection (Wang, WO 97/46697). The CD4/coreceptor cell surface complex may play dual roles in mediating HIV infection and pathogenesis: (1) as a T cell surface receptor for HIV binding, cell fusion and entry by HIV; or (2) as an HIV suppressive factor.

However effective as agents for the inhibition of HIV infection, the above cell-directed antagonists or antibodies, including highly neutralizing antibodies with specificity for the host cell CD4/coreceptor complex, cannot be used as preventative vaccines. They are agents for passive immunization. For efficacy, these agents must be frequently administered so as to maintain serum concentrations sufficient for full receptor occupancy. A vaccine that acts by inducing an active anti-self antibody response against the CD4/coreceptor complex, by active immunization, would be preferable for protective immunity. Such a vaccine, if it can be developed, would provide effective and long term protection from infection by the infrequent and convenient administration of small quantities of immunogen.

For efficacy, the immunogenic components of such a vaccine must mimic relevant sites on the host cell receptor/coreceptor complex with fidelity sufficient to evoke cross-inhibitory antibodies, while retaining site-specificity sufficient to avoid adverse immunosuppression. The identification of such sites for mimicry by synthetic antigens has not been disclosed by the available anti-cell antibodies which neutralize HIV, including anti-CD4 antibodies with neutralizing activity. For example, a anti-CD4 monoclonal antibody reported to be neutralizing (Burkly et al., *J Immunol*, 1992; 149:1779) and the broadly neutralizing anti-CD4/coreceptor monoclonal antibody reported by Wang (WO 97/46697) recognize discontinuous conformational sites on CD4 that cannot be readily duplicated. Also, the reproduction of useful host cell antigenic target sites as portions of long recombinant immunogens cannot be readily applied as a means to avoid the need for exact knowledge of the vulnerable sites. Most antibodies raised by immunization with CD4 lack useful specificities (Davis et al., *Nature*, 1992; 358:76). For example, high titer hyperimmune antiserum to rsCD4 was devoid of neutralizing activity for primary isolates of HIV (WO 97/46697). Moreover, antibodies with broad reactivity for extensive regions of a T cell antigen are expected to be overly immunosuppressive, in contrast to a site-specific antibody (Reimann et al., *AIDS Res. Hum Retroviruses*, 1997; 13: 933). In addition, although extensive mapping studies of CD4 have yielded a structure function map for the molecule (Sattentau et al., *Science*, 1986, 234:1120; Peterson and Seed, *Cell*, 1988, 54:65; Jameson et al., *Science*, 1988, 240:1335; Sattentau et al., *J Exp. Med.*, 1989, 170:1319; Hasunuma et al., *J Immunol*, 1992, 148:1841; Burkly et al., *J Immunol*, 1992, 149:1779; Davis et al., *Nature*, 1992, 358:76), this mapping does not provide for structural models of sufficient precision for prediction of vulnerable effector sites that are duplicable as synthetic peptides. The available models for CD4 do not disclose useful CD4-based immunogens.

Furthermore, however effective as agents for the inhibition of HIV infection, the cell-directed antagonists or antibodies previously discussed, such as the highly neutralizing antibodies with specificity for the host cell receptor/coreceptor complex (WO 97/46697), are not immunogens and cannot be used as preventative vaccines. They are agents for passive immunization only. A vaccine that acts by inducing an active anti-self antibody response against the receptor/coreceptor complex by active immunization, which would provide effective and long term protection from infection via the infrequent and convenient administration of small quantities of immunogen, would be far more preferable.

For efficacy, the immunogenic components of such an immunogenic composition must comprise a "B cell" epitope that mimics relevant sites on the host cell receptor/coreceptor complex with fidelity, or, a neighboring site if a mimetic peptide epitope cannot be identified, sufficient to evoke cross-inhibitory antibodies while retaining site-specificity sufficient to avoid adverse immunosuppression. The identification of such sites for mimicry by synthetic antigens has been difficult as the broadly neutralizing anti-receptor/coreceptor monoclonal antibodies reported previously recognize discontinuous conformational sites on CD4 that cannot be readily duplicated (WO 97/46697). Also, the reproduction of useful host cell antigenic target sites as portions of long recombinant immunogens cannot be readily applied as a means to avoid the need for exact knowledge of the vulnerable sites. For example, high titer hyperimmune antiserum to rsCD4 is devoid of neutralizing activity for primary isolates of HIV (WO 97/46697). The available 3D model for CD4 (as shown in http:www.pdb.bnl.gov/pdb.bin/pdbids) does not disclose useful immunogens for the host cell surface CD4/coreceptor complex. There remains a need for CD4/coreceptor immunogens, of relevant and safe site-specificity.

In addition to appropriate site-specificity, the receptor/coreceptor immunogens of an effective HIV vaccine must be highly immunostimulatory so as to evoke antibody responses of sufficient level for protection. These immunogens must also be designed to overcome the strong tolerance exhibited towards self molecules. Thus, there also remains a need for immunogens of sufficient immunopotency.

It is an object of the present invention to provide peptide compositions, having the desired site-specificity and immunopotency, as immunogens for the prevention of HIV infection.

Improved immunogenicity and appropriate specificity for the useful synthetic peptide immunogens of the present invention have been accomplished through incorporation of a collection of methods for the identification and design of synthetic peptide immunogens. These methods include: (1) an effective procedure for the identification of an effective high affinity target epitope; (2) the means for stabilization of the conformational features of that target site on a synthetic peptide by the introduction of cyclic constraints, so as to maximize cross-reactivity to the native molecule; (3) the means to augment the immunogenicity of the B cell target epitope by combining it with a site comprising a broadly reactive promiscuous T helper cell (Th) epitope; and (4) the means of enlarging the repertoire of T cell epitopes by application of combinatorial peptide chemistry and thereby further accommodate the variable immune responsiveness of an outbred population.

Synthetic peptides have been used for "epitope mapping" to identify immunodominant determinants or epitopes on the surface of proteins for the development of new vaccines and diagnostics. Epitope mapping employs a series of overlapping peptides corresponding to regions on the protein of interest to identify sites which participate in antibody-immunogenic determinant interaction. Commonly, epitope mapping employs peptides of relatively short length to precisely detect linear determinants. A fast method of epitope mapping known as PEPSCAN is based on the simultaneous synthesis of hundreds of overlapping peptides, of lengths of 8 to 14 amino acids, coupled to solid supports. The coupled peptides are tested for their ability to bind antibodies. The PEPSCAN approach is effective in localizing linear determinants, but not for the identification of epitopes needed for mimicry of discontinuous effector sites such as the HIV receptor/coreceptor binding site (Meloen et al., *Ann Biol. Clin.,* 1991; 49:231–242). An alternative method relies on a set of nested and overlapping peptides of multiple lengths ranging from 15 to 60 residues. These longer peptides can be reliably but laboriously synthesized by a series of independent solid-phase peptide syntheses, rather than by the rapid and simultaneous PEPSCAN syntheses. The resulting set of nested and overlapping peptides can then be used for analyses of antibody binding in systems such as experimental immunizations and natural infections, to identify long peptides which best present immunodominant determinants, including simple discontinuous epitopes. This method is exemplified by the studies of Wang for the mapping of immunodominant sites from HTLV I/II (U.S. Pat. No. 5,476,765) and HCV (U.S. Pat. No. 5,106,726); and it was used for the selection of a precise position on the gp120 sequence for optimal presentation of an HIV neutralizing epitope (Wang et al., *Science,* 1991; 254:285–288).

Peptide immunogens are generally more flexible than proteins and tend not to retain any preferred structure. Therefore it is useful to stabilize a peptide immunogen by the introduction of cyclic constraints. A correctly cyclized peptide immunogen can mimic and preserve the conformation of a targeted epitope and thereby evoke antibodies with cross-reactivities for that site on the authentic molecule. For example, a loop structure present on an authentic epitope can be more accurately duplicated on a synthetic peptide by the addition of advantageously placed cysteine residues followed by cyclization through the sulfhydryl groups (Moore, Chapter 2 in *Synthetic Peptides: A User's Guide*, ed. Grant, WH Freeman and Company: New York, 1992, pp. 63–67).

Another important factor affecting the immunogenicity of a peptide immunogen derived from a receptor/coreceptor complex is the presentation of this peptide to the immune system by T helper cell epitopes that react with a host's T-helper cell receptors and Class II MHC molecules (Babbitt et al., *Nature,* 1985; 317:359–361). T helper epitopes (Th) are often provided by carrier proteins with concomitant disadvantages due to the difficulties for the manufacture of well-defined peptide-carrier conjugates, misdirection of most antibody response to the carrier, and carrier-induced epitopic suppression (Cease, *Intern Rev Immunol,* 1990; 7:85–107; Schutze et al., *J Immunol,* 1985; 135:2319–2322). Alternatively, T cell help may be stimulated by synthetic peptides comprising Th sites. Thus, Class II Th epitopes termed promiscuous Th evoke efficient T cell help and can be combined with synthetic B cell epitopes that by themselves are poorly immunogenic to generate potent peptide immunogens (U.S. Pat. No. 5,759,551). Well-designed promiscuous Th/B cell epitope chimeric peptides are capable of eliciting Th responses and resultant antibody responses targeted to the B cell site in most members of a genetically diverse population expressing diverse MHC haplotypes. Promiscuous Th can be provided by specific sequences derived from potent foreign antigens, such as for example measeles virus F protein, hepatitis B virus surface antigen, and *Chlamydia trachomatis* major outer membrane protein (MOMP). Many known promiscuous Th have been shown to be effective in potentiating a poorly immunogenic peptide corresponding to the decapeptide hormone (U.S. Pat. No. 5,759,551).

Promiscuous Th epitopes range in size from about 15 to about 40 amino acid residues in length (U.S. Pat. No. 5,759,551), and often share common structural features and may contain specific landmark sequences. For example, a common feature is amphipathic helices, which are alpha-helical structures with hydrophobic amino acid residues dominating one face of the helix and with charged and polar resides dominating the surrounding faces (Cease et al., *Proc Natl Acad Sci USA*, 1987; 84:4249–4253). Th epitopes frequently contain additional primary amino acid patterns such as a Gly or charged residue followed by two to three hydrophobic residues, followed in turn by a charged or polar All members of the SSAL are produced simultaneously in a single solid-phase peptide synthesis in tandem with the targeted B cell epitope and other sequences. The Th library sequence maintains the structural motifs of a promiscuous Th and accommodates reactivity to a wider range of haplotypes. For example, the degenerate Th epitope described as SSAL1TH1 was modeled after a promiscuous epitope taken from the F protein of measles virus (Partidos et al., 1991). SSAL1TH1 was used in tandem with an LHRH target peptide. Like the measles epitope, SSAL1TH1 follows the Rothbard sequence and the 1, 4, 5, 8 rule:

```
1               5                    10                   15
Asp-Leu-Ser-Asp-Leu-Lys-Gly-Leu-Leu-Leu-His-Lys-Leu-Asp-Gly-Leu   SEQ ID NOS:61

Glu Ile         Glu Ile Arg      Ile Ile Ile       Arg Ile Glu       Ile   SEQ ID NOS:62

Val             Val          Val Val Val           Val           Val   SEQ ID NOS:63

Phe             Phe          Phe Phe Phe           Phe           Phe   SEQ ID NOS:64
``` residue. This pattern defines what are called Rothbard sequences. Also, Th epitopes often obey the 1, 4, 5, 8 rule, where a positively charged residue is followed by hydrophobic residues at the fourth, fifth and eighth positions after the charged residue, consistent with an amphipathic helix having positions 1, 4, 5 and 8 located on the same face. Since all of these structures are composed of common hydrophobic, charged and polar amino acids, each structure can exist simultaneously within a single Th epitope (Partidos et al., *J Gen Virol*, 1991; 72:1293–99). Most, if not all, of the promiscuous T cell epitopes contain at least one of the periodicities described above. These features may be incorporated into the designs of "idealized artificial Th sites".

Promiscuous Th epitopes derived from foreign pathogens include as examples, but are not limited to, hepatitis B surface and core antigen helper T cell epitopes (HB$_s$ Th and HB$_c$ Th), pertussis toxin helper T cell epitopes (PT Th), tetanus toxin helper T cell epitopes (TT Th), measles virus F protein helper T cell epitopes (MV$_F$ Th), *Chlamydia trachomatis* major outer membrane protein helper T cell epitopes (CT Th), diphtheria toxin helper T cell epitopes (DT Th), *Plasmodium falciparum* circumsporozoite helper T cell epitopes (PF Th), *Schistosoma mansoni* triose phosphate isomerase helper T cell epitopes (SM Th), and *Escherichia coli* TraT helper T cell epitopes (TraT Th). The pathogen-derived Th were listed as SEQ ID NOS:2–9 and 42–52 in U.S. Pat. No. 5,759,551; as Chlamydia helper site P11 in Stagg et al., *Immunology*, 1993; 79; 1–9; and as HBc peptide 50–69 in Ferrari et al., *J Clin Invest*, 1991; 88: 214–222.

Useful Th sites may also include combinatorial Th that incorporate selected degenerate sites into the design of the idealized Th sites. In Wang et al.(WO 95/11998), a particular class of a combinatorial epitope was designated as a "Structured Synthetic Antigen Library" or SSAL. A Th constructed as an SSAL epitope is composed of positional substitutions organized around a structural framework of invariant residues. The sequence of the SSAL is determined by aligning the primary amino acid sequence of a promiscuous Th, retaining relatively invariant residues at positions responsible for the unique structure of the Th peptide and providing degeneracy at the positions associated with recognition of the diverse MHC restriction elements. Lists of invariant and variable positions and preferred amino acids are available for MHC-binding motifs (Meister et al., *Vaccine*, 1995; 13:581–591).

Charged residues Glu or Asp are added at position 1 to increase the charge surrounding the hydrophobic face of the Th. The hydrophobic face of the amphipathic helix is then maintained by hydrophobic residues at 2, 5, 8, 9, 10, 13 and 16, with variability at 2, 5, 8, 9, 10, 13 and 16 to provide a facade with the capability of binding to a wide range of MHC restriction elements. The net effect of the SSAL feature is to enlarge the range of immune responsiveness to an artificial Th (WO 95/11998).

Peptide immunogens that have been designed with the peptide technologies and peptide design elements discussed above, i.e., precise epitope mapping, cyclic constraint, and the incorporation of promiscuous Th epitopes or idealized promiscuous Th, and idealized SSAL Th epitopes, are the basis for the effective synthetic receptor/coreceptor complex vaccines for HIV of the present invention. Such peptides are preferred for appropriate targeting and safety due to effective presentation of a portion of the HIV receptor/coreceptor binding site by optimized positioning and cyclization, and for immunopotency due to broadly reactive Th responsiveness.

SUMMARY OF THE INVENTION

The peptide compositions of the present invention comprise one or more peptide immunogens that have been designed with the peptide technologies and peptide design elements discussed above. As such, the peptide compositions are the basis in a vaccine for effective prevention and treatment of HIV infection and immune disorders. The component peptides of the invention are preferred for their presentation of neutralizing receptor/coreceptor effector sites from the CDR2-like domain of CD4. These peptides evoke effective antibody responses by (1) their optimized site-specificity, obtained via precise epitope mapping of the CDR2-like domain, with consideration for native conformation and constrained conformations via cyclization, and by (2) their broadly reactive Th responsiveness.

According to the present invention, one or more peptides which independently comprise either of two peptide sequences corresponding to the effector sites located on the CDR2 domain of CD4, or immunologically functional analogs thereof, are provided as a peptide composition.

In addition, the target sites of the peptides of the invention are rendered more immunogenic via covalent linkage to a carrier protein through chemical coupling, or more preferably via covalent linkage to synthetic immunostimulatory elements (such as promiscuous Th epitopes), through chemical coupling or more preferably by direct peptide synthesis. Specific examples of carrier protein and immunostimulatory elements are provided, e.g., keyhole limpet hemocyanin (KLH) carrier, modified pertussis enterotoxin A (PEA), Th epitopes (e.g., SEQ ID NO.:6), and general immunostimulatory peptides (e.g., the invasin peptide (Inv) of Yersinia (SEQ ID NO.:7)).

Completely synthetic peptides of the invention may be represented by the formulas:

$$(A)_n\text{-}(Th)_m\text{-}(B)_o\text{-}(CD4\text{-}CDR2 \text{ antigen peptide})\text{-}X$$

or $$(A)_n(CD4\text{-}CDR2 \text{ antigen peptide})\text{-}(B)_o\text{-}(Th)_m\text{-}X$$

or $$(CD4\text{-}CDR2 \text{ antigen peptide})\text{-}(B)_o\text{-}(Th)_m\text{-}(A)_n\text{-}X$$

or $$(Th)_m\text{-}(B)_o\text{-}(CD4\text{-}CDR2 \text{ antigen peptide})\text{-}(A)_n\text{-}X$$

wherein:
  each A is independently an amino acid, or a general immunostimulatory peptide;
  each B is independently an amino acid or other chemical linkage; X is an amino acid α-COOH or α-COHN$_2$;
  Th is a helper T cell epitope or an immune enhancing homolog or segment thereof;
  "CD4-CDR2 antigen peptide" is a peptide antigen that evokes antibodies that react with CD4 surface complex;
  n is from 1 to about 10;
  m is from 1 to about 4; and
  o is from 0 to about 10.

The peptide compositions of the present invention comprise peptide immunogens from about 30 to about 115 amino acid residues, preferably from about 40 to about 90 amino acid residues and more preferably from about 50 to about 80 amino acid residues.

The compositions of the present invention optionally further comprise adjuvants and/or delivery vehicles and other ingredients routinely incorporated with vaccine formulations. The present invention provides instructions for dosage such that immunotherapeutic antibodies directed against the targeted CD4-CDR2 effector sites are generated.

The present invention provides, for the first time, synthetic peptides capable of eliciting antibodies in mammals that are protective against infection by primary isolates of HIV from multiple clades.

The antibody response to the peptide compositions of the invention provides protection or therapy against HIV infection of a host by: (1) blocking HIV binding to CD4-expressing cells, (2) blocking HIV-induced syncytia formation between CD4-expressing cells, (3) neutralizing effectively in vitro infection of CD4 positive cells by primary isolates from all clades of HIV type 1 and HIV type 2, and (4) preventing infection by primary isolates of HIV; when the host is administered a vaccine formulation comprising a peptide composition of the present invention.

The peptide compositions are useful for the prevention and treatment of HIV infection by primary isolates of all clades of HIV-1 and primary isolates of HIV-2 as well as for treatment of undesirable CD4 cell-mediated immune responses such as transplant rejection, and autoimmune disorders such as rheumatoid arthritis, systemic lupus erythematosis, and psoriasis.

BRIEF DESCRIPTION OF THE DRAWINGS

FIG. 1 depicts the amino acid sequence of human CD4 (SEQ ID NO. 1), a part of the host cell antigen CD4/coreceptor complex, as deduced from nucleic acid sequence. The amino acids are represented by the standard single letter codes as follows:

Ala: A Cys: C  His: H Met: M  Thr: T Arg: R   Gln: Q

Ile: I Phe: F  Trp: W Asn: N  Glu: E Leu: L   Pro: P

Tyr: Y Asp: D  Gly: G Lys: K  Ser: S Val: V

The numbering system is that of Littman et al. (*Cell,* 1988, 55:541. The underlined region (AA27–AA66) is the region from which the CD4-CDR2 antigen peptides of the invention are derived.

DETAILED DESCRIPTION OF THE INVENTION

As used herein, "primary isolates of human immunodeficiency virus type 1 (HIV-1)" are obtained by limited cultivation, of up to five passages, of patient peripheral blood mononuclear cells (PBMCs) or plasma with uninfected PBMCs. The primary isolates can be distinguished from TCLA laboratory strains such as IIIb/LAI, SF2 and MN which have been passaged over time in human T-lymphoid cell lines. First, most primary isolates do not readily grow in T cell lines and they display both syncytium inducing (SI) and non-syncytium inducing phenotypes (NSI). For example, many SI primary isolates that induce syncytium formation in PBMC culture will replicate in the especially HIV-sensitive MT2 T cell lines, but few replicate in less permissive T cell lines such as CEM or H9. NSI primary isolates will replicate only in primary T cells. Second, they differ from TCLA strains in their sensitivity to in vitro neutralization by recombinant soluble forms of the viral receptor protein CD4 (rsCD4) (Daar et al., *PNAS USA,* 1990, 87:6574–6578). Third, the laboratory-adapted strains are sensitive to neutralization by antibodies with specificities for the viral envelope, while primary isolates are resistant (Sawyer et al., *J Virol,* 1994, 68:1342; Mascola et al., *J Infect Dis,* 1996, 173:340).

As used herein, "CD4" means any CD4 protein encoded by a naturally occurring CD4 gene. CD4 was initially described as a cell surface marker for T-helper lymphocytes. CD4 was subsequently found to be expressed sparsely on monocytes, Langerhans, microglial cells, and subsets of B cells. The CD4 molecule was found also to participate directly in activation of antigen-specific T helper cells through its function as a receptor for the MHC class II molecule. In 1984, human CD4 was found to be the receptor for HIV (Dalgleish et al., *Nature,* 1984, 312:763). Binding of HIV envelope glycoprotein, gp120, to CD4 represents the initial step in viral entry into the target cell. The amino acid sequence for human CD4 is incorporated herein from Maddon et al. (*Cell,* 1985; 42:93; and, Littman et al., *Cell,* 1988; 55:541) and shown as FIG. 1 and SEQ ID NO:1.

As used herein, "recombinant soluble CD4" or "rsCD4" is a polypeptide expressed by recombinant microorganisms or cells consisting of $AA_1$–$AA_{375}$ of human CD4 (FIG. 1, SEQ ID NO:1).

As used herein, "surface CD4 complex" or "surface complex comprising CD4" refers to intact native CD4 protein as it appears in its natural context on the surface of mammalian cells, together with and/or complexed to any associated membrane proteins.

As used herein, the term "immunogen" relates to a peptide composition which, when administered to a host, is capable of inducing antibodies against target effector sites present on the CDR2 domain of CD4 (SEQ ID NOS:2 and 3), leading to high titer antibodies which have broad neutralizing activities against primary isolates from all clades of HIV type 1 (HIV-1) and type 2 (HIV-2). The CDR2-CD4 target sites are shown in FIG. 1 by underlining and listed as SEQ ID NOS:2 and 3.

A "CD4-CDR2 antigen peptide", according to the present invention, is between about 25 and about 50, preferably between about 30 and about 46, amino acids in length, and contains two cysteine residues separated by an intervening sequence of 28 to 40 amino acid residues. The intervening sequence may be any contiguous portion of the sequence represented by residues 27 to 66 of SEQ ID NO:1, or may be an immunologically functional homologue of residues 27 to 66 of SEQ ID NO:1.

A peptide conjugate, as used herein, refers to a molecule which comprises a CD4-CDR2 antigen peptide covalently attached to a Th helper epitope peptide, by any means other than direct peptide synthesis of the molecule. Examples of covalent coupling of a CD4-CDR2 antigen peptide with a Th epitope peptide to form a peptide conjugate are thiol-haloacetamide coupling, thiol-maleimide coupling, thiol-thiol interchain disulfide bond formation, and the like.

A "peptide immunogen" as used herein refers to a peptide or peptide conjugate, comprising a CD4-CDR2 antigen peptide covalently linked to a Th epitope peptide, optionally further comprising general immunostimulatory peptides, linkers, and spacers as described further herein; and having the ability to evoke antibodies to the CD4-CDR2 antigen peptide.

The term "homolog" as used herein refers to a peptide having essentially the same amino acid sequence, with conservative substitutions of up to about 10% of the amino acids. Conservative substitutions are those wherein one amino acid is replaced by another, preferably from the same class (e.g., hydrophobic, polar, charged, etc.), without significantly altering the properties of the peptide. Homologs may also have insertions or deletions of amino acids that do not significantly alter the immunological properties of the peptide. Homologs may be artificially obtained, or may be found as naturally-occurring variants of the peptide sequences presented herein.

Immunologically functional homologs are homologs which induce essentially the same reaction from the immune system, e.g. T-cell responsiveness, B-cell responsiveness, or induction of antibodies against a given antigen.

This invention is directed to the use of novel peptide compositions as immunogens. The immunogen is useful for the generation, by active immunization, of high titer antibodies directed against the effector sites (SEQ ID NOS:2 and 3) on the CDR2 domain of CD4 in mammals including humans, for prevention and treatment of immunodeficiency virus infection as well as for treatment of undesirable CD4+ cell-mediated immune responses such as transplant rejection, and autoimmune disorders such as rheumatoid arthritis, systemic lupus erythematosis, and psoriasis.

Such interventions employed in the prevention and treatment of HIV infection and immune disorders through the use of specific CD4-reactive antibodies, i.e. a kind of immunotherapy, can be achieved passively, through prophylactic treatment with specific "site-directed" antibodies to a site on the CDR2-like domain of CD4. More preferably, as described herein, therapy can be effected through active immunization, by inoculating the host with a composition comprising one or more peptide immunogens of the present invention. These immunogens elicit the production by the host of its own site-directed CD4-CDR2 reactive antibodies, which have broad neutralizing activities against primary isolates from all clades of HIV type 1 (HIV-1) and type 2 (HIV-2). It is believed that active immunization will provide a more effective and longer lasting form of protection than will passive immunization.

The target sites on the CDR2-like domain of the human CD4 (SEQ ID NOS:2 and 3) are restricted to a cyclic conformation by the addition of cysteine residues to the N and C termini (SEQ ID NOS:4 and 5). Such target sites may also include immunologic homologs of SEQ ID NOS:4 and 5 that comprise 1–5 additional amino acids taken from either terminus of SEQ ID NOS:2 and 3, provided that the single disulfide loop structure is preserved (e.g., SEQ ID NOS:10 and 11).

They are further modified into immunogenic CD4-CDR2 antigen peptides by chemical coupling to a carrier protein, for example, keyhole limpet hemocyanin (KLH) and modified pertussis enterotoxin A (PEA). A deficiency of such "CD4-CDR2 antigen peptide-carrier protein" based vaccines are (1) the weak immunogenicities of the target antigenic sites, an inherent problem associated with almost all self-antigens; (2) the large portion of the non-functional antibodies directed against the carrier proteins and (3) the potential for carrier-induced epitopic suppression.

It is therefore preferable to render the peptides immunogenic by the tandem addition of chemically defined promiscuous Th and/or other immunostimulatory peptides, through chemical coupling or preferably through direct peptide synthesis. The preferred immunogens of the present invention minimize the generation of irrelevant antibodies to elicit a more focused immune response to the "target sequences". The desired antibodies have reactivity to CD4 surface complex, without producing undesirable side effects which may complicate the immunotherapy process for the prevention and treatment of HIV infection and immune disorders. Moreover, the site-specific antibodies targeted to the desired sites can be more broadly generated in a genetically diverse host population by the use of promiscuous Th. These antibody responses lead to high titer antibodies which have broad neutralizing activities against primary isolates from all clades of HIV type 1 (HIV-1) and type 2 (HIV-2).

The present invention is also directed to a method of using said peptide compositions as immunogens for prevention and treatment of immunodeficiency virus infection as well as for treatment of undesirable CD4 cell-mediated immune responses such as transplant rejection, and autoimmune disorders such as rheumatoid arthritis, systemic lupus erythematosis, and psoriasis.

Antibodies which are specific for host cell surface receptor/coreceptor complex comprising CD4, as distinguished from antibodies specific for rsCD4, probably interact with the immune system in several ways:

first, they may block the CD4-class II interaction between CD4-expressing T cells and other activated T cells, B cells, or monocytes;

second, they may deliver signals to T cells, thus inhibiting normal CD4+ T-cell mediated immunoregulatory functions;

third, they may induce cell death of CD4-expressing cells by apoptosis when triggered by a simultaneous engagement of the T cell receptor molecules; and fourth, they block interactions between CD4 and HIV, which inhibits HIV-mediated immunopathology.

Antibodies to the surface complex comprising CD4 are good candidates to prevent and treat HIV infection and HIV-associated diseases including AIDS. On a more general level, antibodies to surface CD4 complex may be useful to prevent or cure undesirable immune responses mediated by CD4-expressing T cells, such as transplant rejection, and autoimmune diseases such as rheumatoid arthritis, systemic lupus erythematosis, or psoriasis.

The properties of the antibodies generated by the peptide compositions of the present invention are summarized here based on the results obtained in Examples 1–3:

1. Binding to rsCD4 in an ELISA assay;
2. Binding to CD4-expressing cells in an immunofluorescent assay; and
3. Neutralizing neutralization-resistant HIV primary isolates in an in vitro microplaque assay.

Antibodies with these characteristics are especially useful in prevention and treatment in humans of diseases caused by infectious agents whose primary targets are CD4-positive cells. Accordingly, the present invention provides peptide compositions as immunogens, useful for preventing and treating diseases in humans caused by infectious agents whose primary targets are CD4 positive cells, particularly the HIV-related diseases including all stages of AIDS. The present invention also provides methods of using these antibody compositions.

The peptide compositions of the present invention comprise peptide immunogens which incorporate either of two peptide sequences corresponding to target effector sites located on the CDR2-like domain of CD4 (SEQ ID NOS:2 and 3), or immunologically functional homologs thereof. The immunogens are characterized by their evocation of neutralizing antibodies against the CD4/coreceptor effector sites from the CDR2 domain of CD4. The immunogens evoke protective antibody responses by virtue of their optimized site-specificity, obtained via (1) precise epitope mapping, (2) consideration of native conformation and constrained conformations via cyclization; and by their broadly reactive Th responsiveness.

Specifically, target sites are taken from the CDR2-like domain of the native human CD4 sequence. The amino acid sequence for human CD4 is incorporated herein from Maddon et al. (*Cell,* 1985; 42:93; and, Littman et al., *Cell,* 1988; 55:541) and shown as FIG. 1 and SEQ ID NO:1. The CD4-CDR2 target sites are shown underlined in FIG. 1 and are listed as SEQ ID NOS:2 and 3. The peptide compositions of the present invention are preferably produced as synthetic peptides comprising the target sites (SEQ ID NOS:2 and 3), in which the targets have been modified from their native sequences by the insertion of cysteine residues at or near both the N terminus and C terminus, so as to facilitate the formation of cyclic peptides (e.g., SEQ ID NOS:4 and 5).

The peptide compositions of the invention also comprise immunologic homologs of SEQ ID NOS:4 and 5 that may comprise 1–5 additional amino acids taken from either terminal of SEQ ID NOS:2 and 3 (e.g., SEQ ID NOS:10 and 11), provided that the single disulfide loop structure is preserved. The target site may also include immunologically functional homologs comprising a cyclic peptide in the range of from about 25 to about 50 amino acids, having a contiguous amino acid sequence derived from SEQ ID NOS:2 and 3. The cyclic structure is an essential element of the invention, as peptides comprising linear counterparts of the target sites do not elicit antibodies with neutralizing activity against primary isolates of HIV.

In addition, the target site of the peptides of the invention are rendered immunogenic via covalent linkage to a carrier protein through chemical coupling, or more preferably via direct chemical peptide synthesis, to synthetic immunostimulatory elements such as for example promiscuous Th epitopes derived from pathogenic viruses and bacteria, artificial promiscuous Th epitopes, and general immunostimulatory peptides. Specific examples of carrier protein and immunostimulatory elements are provided, e.g., keyhole limpet hemocyanin (KLH) carrier protein, modified pertussis enterotoxin A (PEA) carrier protein, a Th from hepatitis B virus surface antigen (SEQ ID NO:8), an artificial Th (e.g., SEQ ID NO.:6), and a general immunostimulatory invasin peptide (Inv) from Yersinia (SEQ ID NO.:7).

Completely synthetic peptides of the invention may be represented by the formulas:

$(A)_n\text{-}(Th)_m\text{-}(B)_o\text{-}(\text{CD4-CDR2 antigen peptide})\text{-}X$ or $(A)_n(\text{CD4-CDR2 antigen peptide})\text{-}(B)_o\text{-}(Th)_m\text{-}X$ or $(\text{CD4-CDR2 antigen peptide})\text{-}(B)_o\text{-}(Th)_m\text{-}(A)_n\text{-}X$ or $(Th)_m\text{-}(B)_o\text{-}(\text{CD4-CDR2 antigen peptide})\text{-}(A)_n\text{-}X$ wherein:

each A is independently an amino acid, α-NH$_2$, or a general immunostimulatory peptide;

each B is independently chosen from the group consisting of amino acids,—NHCH(X)CH$_2$SCH$_2$CO—, —NHCH(X)CH$_2$SCH$_2$CO(ε-N)Lys-, —NHCH(X)CH$_2$S-succinimidyl(ε-N)Lys-, and —NHCH(X)CH$_2$S-(succinimidyl)-;

X is an amino acid α-COOH or α-CONH$_2$;

Th is a helper T cell epitope or an immune enhancing homolog or segment thereof;

"CD4-CDR2 antigen peptide" is as defined above, and is preferably SEQ ID NO:4 or SEQ ID NO:5, or a crossreactive and immunologically functional homolog thereof;

n is from 1 to about 10;

m is from 1 to about 4; and o is from 0 to about 10.

The peptide compositions of the present invention comprise peptide immunogens from about 30 to about 115 amino acid residues, preferably from about 40 to about 90 amino acid residues and more preferably from about 50 to about 80 amino acid residues.

When A is an amino acid, it can be any naturally occurring or non-naturally occurring amino acid. Non-naturally occurring amino acids include, but are not limited to, D-amino acids, β-alanine, ornithine, norleucine, norvaline, hydroxyproline, thyroxine, γ-amino butyric acid, homoserine, citrulline and the like. Moreover, when m is greater than one, and two or more of the A groups are amino acids, then each amino acid may be independently the same or different.

When A is an invasin domain, it can be an immune stimulatory epitope from the invasin protein of a Yersinia species. This immune stimulatory property results from the capability of this invasin domain to interact with the β1 integrin molecules present on T cells, particularly activated immune or memory T cells. The specific sequence for an invasin domain found to interact with the β1 integrins has been described by Brett et al (*Eur J Immunol,* 1993; 23:1608).

A preferred embodiment of the invasin domain (Inv) for linkage to a promiscuous Th epitope has been previously described in U.S. Pat. No. 5,759,551, which is incorporated herein by reference. The Inv domain preferably has the sequence: Thr-Ala-Lys-Ser-Lys-Lys-Phe-Pro-Ser-Tyr-Thr-Ala-Thr-Tyr-Gln-Phe (SEQ ID NO:7) or is an immune stimulatory homolog thereof from the corresponding region in another Yersinia species invasin protein. Such homologs may also contain substitutions, deletions or insertions of amino acid residues to accommodate strain to strain variation, provided that the homologs retain immune stimulatory properties. The invasin domain is preferably attached through a spacer, provided by additional amino acids "A", to the Th peptide.

In one preferred embodiment, n is 3 and $(A)_3$ is an invasin domain (Inv), glycine and glycine, in that order.

$(B)_o$ is an optional spacer and comprises amino acids which can be naturally occurring or the non-naturally occurring amino acids as described above. Each B is independently the same or different. The carrier proteins are covalently attached to the peptides with a spacer (e.g. Lys-Lys-Lys) via chemical coupling. The amino acids of $(B)_o$ can also provide a spacer, e.g., Gly-Gly, between the promiscuous Th epitope and the CD4-CDR2 antigen peptide (SEQ ID NOS:4 and 5), in order to evoke efficient antibody responses. In addition to physically separating the Th epitope from the B cell epitope (e.g., SEQ ID NOS:4 and 5) and immunological homologs thereof, a spacer such as Gly-Gly can disrupt any artifactual secondary structures created by the joining of the Th epitope with the CD4-CDR2 antigen peptides, and thereby eliminate interference between the Th and/or B cell responses.

The amino acids of $(B)_o$ can also form a spacer which acts as a flexible hinge that enhances separation of the Th and IgE domains. Examples of sequences encoding flexible hinges are found in the immunoglobulin heavy chain hinge region. Flexible hinge sequences are often proline rich. One particularly useful flexible hinge is provided by the sequence Pro-Pro-Xaa-Pro-Xaa-Pro (SEQ ID NO:9), where Xaa is any amino acid, and preferably aspartic acid. The conformational separation provided by the amino acids of $(B)_o$ permits more efficient interactions between the presented peptide immunogen and the appropriate Th cells and B cells and thus enhances the immune responses to the Th epitope and the antibody-eliciting epitope and their crossreactive and immunologically functional homologs thereof.

Th is a sequence of amino acids (natural or non-natural amino acids) that comprises a Th epitope. A Th epitope can consist of a continuous or discontinuous epitope, hence not every amino acid of Th is necessarily part of the epitope. Th epitopes, including homologs and segments of Th epitopes, are capable of enhancing or stimulating an immune response to the CD4-CDR2 antigen peptides (e.g., SEQ ID NOS:4 and 5, and immunologically functional homologs thereof). Th epitopes that are immunodominant and promiscuous are highly and broadly reactive in animal and human populations with widely divergent MHC types (Partidos et al., 1991; U.S. Pat. No. 5,759,551). The Th domain of the subject peptides has from about 10 to about 50 amino acids and preferably from about 10 to about 30 amino acids. When multiple Th epitopes are present (i.e. m ≧2), then each Th epitope is independently the same or different. Th segments are contiguous portions of a Th epitope that are sufficient to enhance or stimulate an immune response to the CD4-CDR2 antigen peptides (e.g., SEQ ID NOS:4 and 5), and/or to immunologically functional analogs thereof.

Th epitopes of the present invention include those derived from foreign pathogens and provided as examples, but are not limited to, hepatitis B surface and core antigen helper T cell epitopes ($HB_s$ Th and $HB_c$ Th), pertussis toxin helper T cell epitopes (PT Th), tetanus toxin helper T cell epitopes (TT Th), measles virus F protein helper T cell epitopes (MVF Th), *Chlamydia trachomatis* major outer membrane protein helper T cell epitopes (CT Th), diphtheria toxin helper T cell epitopes (DT Th), *Plasmodium falciparum* circumsporozoite helper T cell epitopes (PF Th), *Schistosoma mansoni* triose phosphate isomerase helper T cell epitopes (SM Th), and *Escherichia coli* TraT helper T cell epitopes (TraT Th). Pathogen-derived Th epitopes listed as SEQ ID NOS:2–9 and 42–52 in U.S. Pat. No. 5,759,551; as Chlamydia helper T cell P11 in Stagg et al., *Immunology,* 1993; 79;1–9; and as HBc peptide 50–69 in Ferrari et al., *J Clin Invest,* 1991; 88: 214–222; are incorporated herein by reference.

Th epitopes further include artificial idealized Th, e.g., SEQ ID NO:6, and immunologically functional homologs. Functional Th homologs include immune-enhancing homologs, crossreactive homologs and segments of any of these Th epitopes. Functional Th homologs further include conservative substitutions, additions, deletions and insertions of from one to about 10 amino acid residues in the Th epitope which do not essentially modify the Th-stimulating function of the Th epitope.

Preferred peptide immunogens of this invention are the peptides containing the CD4-CDR2 antigen peptides (e.g., SEQ ID NO:4 or 5, or immunologically functional homologs thereof) and Th epitopes, and optionally a general immunostimulatory site, e.g., Inv (SEQ ID NO:7). In a more preferred embodiment the Th epitope is an $HB_s$ Th, $HB_c$ Th, $MV_F$ Th, PT Th, TT Th, CT Th or HIV Th derived from foreign pathogens or an idealized artificial Th, or functional immunogenic homolog thereof. Optionally, A is a general immunostimulatory peptide, e.g., Inv (SEQ ID NO:7), preferably attached via a Gly-Gly spacer.

The structure of the modified site is based on a peptide sequence taken from the CDR2-like domain of human CD4 (amino acids 27-66 of SEQ ID NO:1), or the homologous sequence from another species. This CD4-CDR2 target site is subjected to the following modifications:

(1) the addition or insertion of a cysteine residue near the N-terminus, (2) the addition or insertion of a cysteine residue near the C-terminus, preferably at or near position 66 or homologous position, and (3) the formation of a disulfide bond between the retained cysteines so as to produce a cyclic structure.

The peptide structures may also comprise 1 to 5 additional amino acids taken from either terminus of the 27–66 or 39–66 segment of CD4, provided that the single disulfide loop cyclic structure is preserved (e.g., SEQ ID NOS:10 and 11). Preferably, any intervening cysteines in the native sequence not intended to be employed for cyclization will be conservatively substituted for, for example with serine.

For example, the human CD4-CDR2 target sites (SEQ ID NOS:2 and 3) are cyclized by means of added cysteines at or near both the N- and C- termini (e.g. SEQ ID NOS:4 and 5) or through an added cysteine at the N-terminus and a cysteine substitution near the C terminus (e.g., substituting Cys for Phe at position 67, to obtain SEQ ID NOS:10and 11). Modified, cyclized, and overlapping CD4-CDR2 antigen peptides with the following sequences

Cys His Trp Lys Asn Trp Asn Gln Ile Lys Ile Leu Gly Asn Gln Gly Ser Phe Leu Thr Lys Gly Pro Ser Lys Leu Asn Asp Arg Ala Asp Ser Arg Arg Ser Leu Trp Asp Gln Gly Asn Cys (SEQ ID NO.:4)

Cys Asn Gln Gly Ser Phe Leu Thr Lys Gly Pro Ser Lys Leu Asn Asp Arg Ala Asp Ser Arg Arg Ser Leu Trp Asp Gln Gly Asn Cys (SEQ ID NO.:5)

Cys His Trp Lys Asn Trp Asn Gln Ile Lys Ile Leu Gly Asn Gln Gly Ser Phe Leu Thr Lys Gly Pro Ser Lys Leu Asn Asp Arg Ala Asp Ser Arg Arg Ser Leu Trp Asp Gln Gly Asn Cys Pro Leu Ile Ile (SEQ ID NO.:10)

and

Cys Asn Gln Gly Ser Phe Leu Thr Lys Gly Pro Ser Lys Leu Asn Asp Arg Ala Asp Ser Arg Arg Ser Leu Trp Asp Gln Gly Asn Cys Pro Leu Ile Ile (SEQ ID NO:11)

are provided by way of example. In these examples, the modified positions are indicated by boldface type.

Antibody that is evoked by peptide immunogens comprising the CD4-CDR2 antigen peptides of the invention is crossreactive with host cell surface receptor/coreceptor complex comprising CD4, and neutralizes primary isolates of HIV. Corresponding target antigenic sites for surface CD4 of other species can be likewise derived from the homologous segments of the relevant species.

Crossreactive and immunologically functional homologs of the CD4-CDR2 antigen peptides (SEQ ID NOS:4, 5, 10 and 11) may further comprise conservative substitutions, additions, deletions, or insertions of from one to about four amino acid residues, provided that the peptide homologs are capable of eliciting immune responses crossreactive with the CD4-CDR2 peptides (SEQ ID NOS:2, 3, 4, and 5) and having neutralizing activity against primary isolates of HIV. Conservative substitutions, additions, and insertions are known to those skilled in the art, and can be readily accomplished with natural or non-natural amino acids as defined herein.

Preferred peptide immunogens of this invention are peptides containing (1) the cyclized modified CD4-CDR2 sites referred to herein as CD4-CDR2 antigen peptides (e.g., SEQ ID NOS:4,5,10 and 1 1) or immunological homologs thereof and (2) Th epitope peptides. The more preferred peptide immunogens are those tandem constructs containing the cyclized CD4-CDR2 antigen peptides (SEQ ID NOS:4,5,10 and 11) or crossreactive and immunologically functional homologs thereof, a spacer (e.g., Gly-Gly); a Th epitope selected from the group consisting of an $HB_s$ Th, $HB_c$ Th, $MV_F$ Th, PT Th, TT Th, an artificial Th (e.g., SEQ ID NO:6), or a homolog thereof; and, optionally, an Inv domain (SEQ ID NO:7) or analog thereof.

The peptide immunogens of this invention can be made by chemical synthesis methods which are well known to the ordinarily skilled artisan. See, for example, Fields et al., Chapter 3 in *Synthetic Peptides: A User's Guide*, ed. Grant, W.H. Freeman & Co., New York, N.Y., 1992, p.77. Hence, peptides can be synthesized using the automated Merrifield techniques of solid phase synthesis with the $\alpha$-$NH_2$ protected by either t-Boc or Fmoc chemistry, and using commercially available side chain protected amino acids. Examples of suitable instruments for peptide synthesis are the Applied Biosystems Peptide Synthesizer Models 430A or 431.

After complete assembly of the desired peptide immunogen, the resin is treated according to standard procedures to cleave the peptide from the resin and deblock the functional groups on the amino acid side chains. The free peptide is purified by HPLC and characterized biochemically, for example by amino acid analysis, by mass spectrometry, and/or by sequencing. Purification and characterization methods for peptides are well-known to those of skill in the art.

Other chemical means to generate the peptide constructs of the invention containing CD4 and Th sites include the ligation of haloacetylated and cysteinylated peptides through the formation of a "thioether" linkage. For example, a cysteine can be added to the C terminus of a Th-containing peptide and the thiol group of the cysteine may be used to form a covalent bond to an electrophilic group (for example, an N-(chloroacetyl) or a maleimide-derivatized $\alpha$- or $\epsilon$-$NH_2$ group of a lysine residue) attached to the N-terminus of a CD4-CDR2 antigen peptide. In this manner, a peptide conjugate composition comprising Th-$(B)_o$-(CD4-CDR2 antigen peptide) or its reverse, (CD4-CDR2 antigen peptide)-$(B)_o$-Th, with or without a general immunostimulatory site, may be obtained, wherein one of the linkers "B" is —NHCH(X)$CH_2SCH_2CO$—, —NHCH(X)$CH_2SCH_2CO$($\epsilon$-N)Lys-, —NHCH(X)$CH_2S$-succinimidyl ($\epsilon$-N)Lys-, or —HCH(X)$CH_2S$-(succinimidyl)-.

The subject immunogen may also be polymerized. Polymerization can be accomplished by reaction of the immunogen with a cross-linking reagent, for example by reaction between glutaraldehyde and the —$NH_2$ groups of lysine residues, using routine methodology.

By another method, the synthetic peptide immunogens can be polymerized or co-polymerized by utilization of an additional cysteine added to the N-terminus of the immunogen. The thiol group of the N-terminal cysteine can be used for the formation of a "thioether" bond with haloacetyl-modified amino acid or a maleimide-derivatized $\alpha$- or $\epsilon$-$NH_2$ group of a lysine residue that is attached to the N-terminus of a branched poly-lysyl core molecule (e.g., $K_2K$, $K_4K_2K$ or $K_8K_4K_2K$). The subject immunogen may also be polymerized as a branched structure through synthesis of the desired peptide construct directly onto a branched poly-lysyl core resin (Wang, et al., *Science,* 1991; 254:285–288).

Alternatively, the longer synthetic peptide immunogens can be synthesized by well-known recombinant DNA techniques. Many standard manuals on DNA technology provide detailed protocols to produce the peptides of the invention. To construct a gene encoding a peptide of this invention, the amino acid sequence is reverse translated into a nucleic acid sequence, preferably using optimized codon usage for the organism in which the gene will be expressed. Next, a synthetic gene is made, typically by synthesizing overlapping oligonucleotides which encode the peptide and any necessary regulatory elements. The synthetic gene is inserted in a suitable cloning vector and recombinants are obtained and characterized. The peptide is then expressed under suitable conditions appropriate for the selected expression system and host. The peptide is purified and characterized by standard methods.

The nucleic acids described above may themselves be useful as components of so-called "DNA vaccines". In this embodiment of the invention, expression of the immunogenic peptides of the invention is induced in the patient's own cells, by introduction into those cells of nucleic acids which encode the peptides, preferably using codons and promoters that optimize expression in human cells. Methods of making and using DNA vaccines are disclosed in U.S. Pat. Nos. 5,580,859, 5,589,466, and 5,703,055; see also WO 97/02840 and W. McDonnell and F. Askari, *New Engl. J. Med.*, 1996, 334:2–45, all of which are incorporated herein by reference. Such methods of making and using the peptides and peptide conjugates of this invention are contemplated to be within the scope of this invention.

The efficacy of the peptide composition of the present invention can be established by injecting animals, for example, guinea pigs, followed by monitoring the humoral immune response to the CD4-CDR2 antigen peptides for the immune sera's ability to neutralize primary isolates of HIV as detailed in the Examples.

Another aspect of this invention provides a vaccine composition comprising an immunologically effective amount of one or more of the peptide immunogens of this invention in a pharmaceutically acceptable delivery system. Such immunogenic compositions are used for prevention and treatment of immunodeficiency virus infection as well as for treatment of undesirable immune responses mediated by CD4-expressing T cells such as transplant rejection, and autoimmune disorders such as rheumatoid arthritis, systemic lupus erythematosis, and psoriasis.

Accordingly, the peptide composition of the invention can be formulated as an immunogenic composition using adjuvants, emulsifiers, pharmaceutically-acceptable carriers or other ingredients routinely provided in vaccine compositions. Adjuvants or emulsifiers that can be used in this invention include alum, incomplete Freund's adjuvant, liposyn, saponin, squalene, L121, emulsigen, monophosphoryl lipid A (MPL), QS21, ISA206, and ISA 720, as well as other known efficacious adjuvants and emulsifiers. Such formulations are readily determined by one of ordinary skill in the art and also include formulations for immediate release and/or sustained release, and for induction of systemic immunity and/or induction of localized mucosal immunity, which may be accomplished by, for example, by immunogen entrapment or by coadministration with microparticles. The present vaccines can be administered by any convenient route including subcutaneous, oral, intramuscular, or other parenteral or enteral route. Similarly the immunogens can be administered as a single dose or multiple doses. Immunization schedules are readily determined by the ordinarily skilled artisan.

The immunogenic composition of the instant invention contains an effective amount of one or more of the peptide immunogens of the present invention and a pharmaceutically acceptable carrier. Such a composition in a suitable dosage unit form generally contains about 0.5 µg to about 1 mg of the immunogen per kg body weight. When delivered in multiple doses, it may be conveniently divided into an appropriate amount per dosage unit form. For example, the initial dose, e.g. 0.2–2.5 mg; preferably 1 mg, of immunogen represented as a peptide composition of the present invention, is to be administered by injection, preferably intramuscularly, followed by repeat (booster) doses. Dosage will depend on the age, weight and general health of the patient as is well known in the vaccine and therapeutic arts.

Vaccines which contain mixtures of the subject peptide immunogens with two or more of the Th epitopes may enhance immunoefficacy in a broader population and thus provide an improved immune response to the CD4-CDR2 antigen peptide (e.g., SEQ ID NOS:4 and 5).

The immune response to the synthetic CD4-CDR2 immunogens of the invention may be improved by delivery through entrapment in or on biodegradable microparticles of the type described by O'Hagan et al. (Vaccine, 1991; 9:768). The immunogens can be encapsulated with or without an adjuvant, and such microparticles can carry an immune stimulatory adjuvant. The microparticles can also be coadministered with the peptide immunogens to potentiate immune responses, including localized mucosal immunity which may be especially applicable to a mucosally transmitted virus such as HIV, and to provide time-controlled release for sustained or periodic responses, for oral administration, and for topical administration.(O'Hagan et al., 1991; and, Eldridge et al., 1991; 28:287).

In order that this invention may be better understood, the following examples are set forth. These examples are for purposes of illustration only, and are not to be construed as limiting the scope of the invention in any manner.

EXAMPLES

The target antigenic site peptides of these Examples were synthesized by the solid-phase method outlined in Example 1. Each peptide can be represented by the formula $(A)_n$-$(Th)_m$-$(B)_o$-(CD4-CDR2 antigen peptide) or $(A)_n$-(CD4-CDR2 antigen peptide)-$(B)_o$-$(Th)_m$, but other formulas as described above are also encompassed within the invention. The CD4 target antigenic site is a cyclized peptide, exemplified by SEQ ID NOS:4, 5, 10 and 11, but immunologically functional homologs comprising a cyclic peptide in the range of from about 25 to about 50 amino acids, having a contiguous amino acid sequence derived from SEQ ID NOS:2 or 3 and up to an additional five amino acid sequence attached to either the N- or C-terminus of the cyclic structure, are intended to be within the scope of the invention.

Each peptide used for these examples has Gly-Gly as the $(B)_o$ spacer between the Th and modified CD4-CDR2 target site immunogenic elements, and some incorporate an optional $(A)_3$ element comprising Inv-Gly-Gly wherein Inv (SEQ ID NO:7) is coupled to the antigenic peptide (e.g., SEQ ID NOS:32–35), but peptides of the invention may also have other spacers (e.g., SEQ ID NO:9) or no spacers. Th epitopes, as exemplified in Table 8, include promiscuous helper sites derived from foreign pathogens such as hepatitis B virus surface and core and measles virus F protein (e.g., SEQ ID NOS:8, 45–47, 38, and 39), and other Th epitopes as shown in Table 8 (SEQ ID NOS:13, 40–44, and 48–58) and artificial Th as shown in Table 9 (e.g., SEQ ID NOS:6, 12 and 36). Peptides of this example also include an optional general immunostimulatory site (e.g., SEQ ID NO:7). Furthermore, the invention is not limited to Inv as the additional immunostimulatory element.

Example 1

Identification of Potential Effector Sites on Surface CD4/Coreceptor Complex

A. Peptide Design

Sites within all four domains of human CD4 along with coreceptor sites representing the four external domains of chemokine receptors, including CC-CKR1, CC-CKR2b, CC-CKR3, CCKR5 and LESTR were selected for mimicry by peptides. As the "epitope" recognized by MAb B4 (WO 97/46697) is conformational in nature, none of the linear peptides derived from the above receptor/coreceptors reacted strongly with MAb B4, although the reactivity of MAb B4 with rsCD4 was significantly enhanced in the presence of certain peptides derived from chemokine coreceptor domains as shown in WO 97/46697.

Despite the lack of strong reactivity of MAb B4 with any single CD4- or chemokine coreceptor-derived peptide, weak MAb B14 reactivities for peptides derived from various regions of CD4 ($AA_1$-$A_{20}$, $AA_{81-92}$, $AA_{60}$-$AA_{109}$, $AA_{118}$-$AA_{165}$, $AA_{235-251}$, $AA_{297}$-$AA_{351}$, or $AA_{361}$-$AA375$) were detected. This prompted a different approach that aimed to design synthetic peptides that would elicit high affinity antibodies reactive with a site(s) neighboring to the conformational one recognized by MAb B4, for inhibition of HIV infection of the target cells.

The sequences of such potential sites scattered throughout all four domains of CD4 and the external domains of various chemokine coreceptors were therefore designed and synthesized as target peptides and rendered into immunogens by constructing peptides where promiscuous Th's derived from HBsAg (SEQ ID NO:8) and Inv (SEQ ID NO:7) were linked to the target sites, as shown in Tables 1 and 2. Specific CD4 sites within these domains were selected for cyclization based on predictions by the Brookhaven 3-dimensional model for human CD4 (http:www.pdb.bnl.gov/pdb.bin/pdbids) of surface-exposed loops. Specified cyclic constraints were installed into these peptides so as to maximize the crossreactions between the target antigenic sites and the native CD4 molecule.

Accordingly, several of the synthetic constructs of Tables 1 and 2 were synthesized with introduced cysteines not found in the native sequence, to produce disulfide bond loops in mimicry of loop structures predicted by the Brookhaven model. In some cases naturally occurring cysteines were substituted with serines so as to prevent the formation of conformations not favored by the model. For chemokine coreceptor-derived peptides, crosslinkage between peptides of external domains 2 and 3, shown in the far right of Table 2, was made via the naturally existing cysteine residues in the respective domains, in mimicry of their native structure.

Sites marked by * in the description column of Table 1 have been so designed with specified cyclization. Other peptide sites are linear. Peptides labeled by "a" in the Form columns of Tables 1 and 2 represent the CD4 or CCKR target antigen site alone. These were used as the substrate antigens for peptide based ELISAs. Peptides marked by "b" were synthesized as target antigenic sites in tandem with the HBs Th site (SEQ ID NO:8) as shown. Peptides marked by "c" are variants of the "b" constructs synthesized in tandem with the Inv domain immunostimulatory peptide (SEQ ID NO:7) as shown in Tables 1 and 2. Peptides designated as "d" were variants of the "b" constructs synthesized in tandem with a second Th peptide, CT P11 Th (SEQ ID NO:13) attached to the N-terminus through a Gly-Gly linker. Peptides marked by "e" were synthesized as the reversal of "b" with Th sites located at the C terminus and the target antigenic site at the N-terminus of the construct. A peptide marked by "g" represents a branched tetrameric peptide with synthesis conducted directly onto a polylysyl core resin. Peptides marked by "x" represent peptides comprising a two-chain structure linked by an inter-disulfide bond via the naturally existing cysteine residues present on the respective chains.

Other Th sites used in the experiments shown in Tables 1 and 2, but not shown here, employed the artificial Th sites "1,4,9 PALINDROMIC" (SEQ ID NO:6) and "Syn Th (1,2,4)" (SEQ ID NO:12). Peptides with the Inv site located at the C terminus, and the CD4-CDR2 antigen at the N terminus (CD4-CDR2 antigen peptide-GG-Th-GG-Inv) were also prepared, but are not shown.

The "b", "c", "d", "e", "x", and "other" Th immunogenic peptides used for the studies of Tables 1 and 2 were also synthesized with Gly-Gly spacers for separation of the target antigenic site from the Th site, and separation of the Th from the Inv or a from a second Th immunostimulatory site. The resulting peptide immunogens were screened as candidate target antigenic sites for their ability to induce in immunized hosts antibodies with the following properties:

1. Binding to the target antigenic site in an ELISA assay;
2. Binding to rsCD4 in an ELISA assay, in the instances of CD4-derived antigenic peptides;
3. Binding in an immunofluorescent assay to T cells that express the cell surface receptor/coreceptor complex comprising CD4; and
4. Neutralizing neutralization-resistant HIV primary isolates in an in vitro microplaque assay.

B. Screening of Candidate Target Antigenic Peptides

1. Synthesis of CD4- and Chemokine Receptor-derived Target Antigenic Peptides

Peptides listed in Tables 1 and 2 in their corresponding "a", "b", "c", "d", "e", or "x" form were synthesized individually by the Merrifield solid-phase synthesis technique on Applied Biosystems automated peptide synthesizers (Models 430, 431 and 433A) using Fmoc chemistry. The preparation of peptide immunogens comprising a structured synthetic antigen library (SSAL) for artificial T cell epitope "(1,4,9 PALINDROMIC) Th" (SEQ ID NO:6) was accomplished by providing a mixture of alternative amino acids for coupling at a given variable position, at the appropriate ratio as specified in the design of SEQ ID NO:6. SSAL peptides having library designs for either the B cell target antigen site or other SSAL Th sites can be synthesized in a like manner. After complete assembly of the desired peptide, the resin was treated according to standard procedure using trifluoroacetic acid to cleave the peptide from the resin and deblock the protecting groups on the amino acid side chains. For cyclic peptides, the cleaved peptide was allowed to stand in 15% DMSO in water for 48 hrs to facilitate intrachain disulfide bond formation between cysteines. The cleaved, extracted and washed peptides were purified by HPLC and characterized by mass spectrometry and reverse phase HPLC.

2. Generation of CD4 and Chemokine Receptor-derived Target Antigenic Site-Specific Immune Sera for Functional Efficacy and Evaluation Immunogenic efficacy of peptide compositions was evaluated as specified by the experimental immunization protocol outlined below followed by serological assays of antibody response.

Standard Experimental Design:

Immunogens:
(1) individual peptide immunogen; or
(2) a mixture comprising an equal molar ratio of peptide immunogens as specified in each protocol.

Dose: 100 µg in 0.5 ml per immunization unless otherwise specified.

Route: intramuscular unless otherwise specified.

Adjuvants:
(1) Freund's Complete Adjuvant(CFA)/Incomplete Adjuvant (IFA);
(2) 0.4% Alum (Aluminum hydroxide); or
(3) other adjuvants as specified. One adjuvant per immunogen per group.

Dose Schedule: 0, 2, and 4 weeks; or 0, 3, and 6 weeks; or as otherwise specified. CFA/IFA groups received CFA week 0, and IFA in subsequent weeks. Alum or other specified adjuvant groups received same formulations for all doses.

Bleed Schedule: weeks 0, 3, 6, and 8, or as otherwise specified

Species: Duncan Hartley guinea pigs

Group Size: 3 guinea pigs/group

Assay: Specific ELISAs for each immune serum's anti-peptide activity. Solid-phase substrates were the corresponding "a" form of target antigenic peptide (e.g., CD4 target antigenic peptide, chemokine receptor derived peptide, etc.)

Blood was collected and processed into serum, and stored prior to titering by ELISA with the target antigenic peptides.

3. Sera and Antibodies

The following serological reagents, either immune sera derived from guinea pigs, or murine or humanized monoclonal antibody were used for evaluations in several serological assays. All guinea pig sera directed against rsCD4, CD4- and chemokine coreceptor-derived target antigenic sites were obtained as described above at various time points after immunization. Other serological reagents were obtained through previous studies or from outside sources as described. These were occasionally incorporated for purposes of comparison.

For example gp anti-gp120 V3 MN (anti-V3 MN) is pooled sera from guinea pigs that had been hyperimmunized with a synthetic peptide antigen corresponding to the hypervariable V3 domain of gp120 from HIV-1 MN (Wang et al., Science, 1991, 254:285–288). GP anti-gp120 V3 library sera is pooled antisera from three guinea pigs hyperimmunized with a complex mixture of peptides representing a SSAL of approximately $10^{13}$ possible HIV-1 V3 sequences (anti-V3 SSAL). The V3 MN and V3 SSAL immunogens used for the guinea pig immunizations were multibranched V3 synthetic peptide immunogens that were used to generate polyclonal antibodies with neutralizing activity for several laboratory strains of HIV-1, as described in Walfield et al. (Chapter 18 in *AIDS Research Reviews*, ed. Koff et al., Marcel Dekker: New York, 1993, pp.345–360).

Another anti-gp120antibody was a recombinant human monoclonal antibody designated IgG1 b12 with specificity for the gp120 binding site for CD4 (anti-gp120CD4-BS) (Burton et al., Science, 1994, 266:1024–1027). IgG1 b12 was generated as an Fab fragment from an antibody-phage display library prepared from bone marrow of a long-term asymptomatic HIV-1 seropositive donor and was converted to a whole human antibody by cloning into a recombinant DNA IgG1 expression vector. It is regarded as the "gold standard" of antibodies for neutralization of diverse HIV primary isolates (Burton et al., supra).

4. Anti-peptide ELISAs

Anti-peptide antibody activities were determined by ELISAs (enzyme-linked immunosorbent assays) using 96-well flat bottom microtiter plates which were coated with the corresponding target antigenic site peptide in "a" form as immunosorbent. Aliquots (100 $\mu$L) of a target antigenic peptide solution at a concentration of 5 $\mu$g/ml were incubated for 1 hour at 37° C. The plates were blocked by another incubation at 37° C. for 1 hour with a 3% gelatin/PBS solution. The blocked plates were then dried and used for the assay. Aliquots (100 $\mu$L) of the test immune sera, starting with a 1:100 dilution in a sample dilution buffer and ten-fold serial dilutions thereafter, were added to the peptide coated plates. The plates were incubated for 1 hour at 37° C.

The plates were washed six times with 0.05% PBS/TWEEN® buffer. 100 $\mu$L of horseradish peroxidase labeled goat-anti-species specific antibody was added at appropriate dilutions in conjugate dilution buffer (Phosphate buffer containing 0.5 M NaCl, and normal goat serum). The plates were incubated for 1 hour at 37° C. before being washed as above. Aliquots (100 $\mu$L) of o-phenylenediamine substrate solution were then added. The color was allowed to develop for 5–15 minutes before the enzymatic color reaction was stopped by the addition of 50 $\mu$L 2N $H_2SO_4$. The $A_{492}$ of the contents of each well was read in a plate reader. ELISA titers, shown as $Log_{10}$ of the reciprocal dilution, were calculated based on linear regression analysis of the absorbances, with cutoff $A_{492}$ set at 0.5. This cutoff value was rigorous as the values for diluted normal guinea pig control samples run with each assay were less than 0.1.5.

5. Determination of Antibody Reactivities with rsCD4, and with CD4-Expressing Cells 5.1 Determination of Anti-CD4 Reactivity by rsCD4 ELISA. Purified recombinant soluble CD4 (rsCD4) was obtained from a commercial source (American Bio-Technologies, Inc. Cambridge, Mass.) and from NIH (USA) AIDS Research and Reference Reagent Program. rsCD4 ELISAs were conducted by coating 96-well microtiter plates by overnight incubation at 4° C. with rsCD4 at 0.25 $\mu$g/ml using 100 $\mu$L per well in 10 mM $NaHCO_3$ buffer, pH 9.5. The rsCD4-coated wells were incubated with 250 $\mu$L of 3% by weight of gelatin in PBS at 37° C. for 1 hr to block non-specific protein binding sites, washed three times with PBS containing 0.05% by volume TWEEN 20 and then dried.

Immune sera or monoclonal antibodies were serially diluted with PBS containing 20% by volume normal goat serum, 1% by weight gelatin and 0.05% by volume TWEEN 20 at dilutions of 1:20 volume to volume unless indicated otherwise. 100 $\mu$L of the diluted sample was added to each of the wells and allowed to react for 1 hr at 37° C. The wells were then washed six times with 0.05% by volume TWEEN 20 in PBS to remove unbound labeled antibodies. 100 $\mu$L of horseradish peroxidase labeled goat anti-mouse IgG or goat anti-guinea pig IgG at a dilution of 1:1000 in 1% by volume normal goat serum, 0.05% by volume TWEEN 20 in PBS was added to each well and incubated at 37° C. for 15 minutes. The wells were washed six times with 0.05% by volume TWEEN 20 in PBS to remove unbound labeled antibody conjugate and reacted with 100 $\mu$L of the substrate mixture containing 0.04% by weight orthophenylenediamine (OPD) and 0.12% by volume hydrogen peroxide in sodium citrate buffer pH 5.0, for 15 minutes. Reactions were stopped by the addition of 100 $\mu\mu$L of 1.0 M $H_2SO_4$ and the absorbance at 492 nm ($A_{492}$) was measured. The reciprocal $Log_{10}$ antibody titer was calculated for the end point reactivity of each test sample, as interpolated by linear regression, as described for the anti-peptide ELISA.

5.2 Determination of Reactivity to CD4-Expressing Cells by Indirect Immunofluorescent Staining. $0.5 \times 10^6$ CD4-expressing cells (e.g. HPB-ALL, MT2 or SUP-T1 cell line cells) per well were washed twice in PBS containing 1% BSA prior to their incubation with the designated immune sera or monoclonal antibodies, at an optimal concentration as determined for each experiment, for 45 minutes at room temperature. After incubation of the cells with the first staining antibody, the cells were washed for an additional two times in the same washing buffer and were incubated with a secondary fluorescein isothiocyanate (FITC)-conjugated goat anti-mouse IgG or (FITC)-conjugated goat anti-species specific IgG reagent at appropriate dilutions (Cappel, Malvern Pa.) for an additional 45 minutes at room temperature. The stained cells were washed again in the same washing buffer and the cells processed for fluorescence analysis by cytofluorograph and/or immunofluorescence microscopy for determination of percentage of stained cells, and intensity of staining.

5.3 Indirect Immunofluorescence Inhibition Assay. For competitive "biotinylated monoclonal antibody B4-T cell" binding inhibition assays employing the indirect immunofluorescence staining technique, cells were first incubated with the interfering reagents or appropriately diluted immune sera and washed twice in the same washing buffer before the addition of biotinylated monoclonal antibody B4. Staining of the CD4-expressing T cells was completed by subsequent incubation with appropriately diluted FITC-avidin followed by additional three washes prior to analysis by cytofluorograph or high resolution fluorescence microscope.

6. Determination of Virus Neutralization by Antibody 6.1 Cells. Human T cell line MT-2 (ATCC 237) was maintained in Dulbecco's modified Eagle medium supplemented with 15% fetal bovine serum as previously described (Hanson et al., *J Clin Microbiol*, 1990, 28:2030–2034). Peripheral blood mononuclear cells (PBMCs) of HIV-1 seronegative donors were isolated from fresh buffy coat units by FICOLL-HYPAQUE gradient separation (Organon Teknika Corp., Durham, N.C.). The resulting PBMCs were stimulated with 0.5% PHA-P (Difco Laboratories, Detroit, Mich.). After 3 to 4 days, the PHA-P-containing medium was removed and the cells maintained in RPMI with 15% fetal bovine serum, 900 µg/ml glutamine, antibiotics, and 5% interleukin-2 (Cellular Products, Inc., Buffalo, N.Y.).

6.2 Viruses. HIV-1 MN is a TCLA strain available as and maintained as a persistently infected H9 cell culture from the National Institutes of Health, Bethesda Md. (NIH AIDS Research and Reference Reagent Program Catalog no. 402), from which were prepared cell-free concentrated stocks. Primary isolates of HIV-1 were prepared from patient PBMCs by PBMC cocultivation. Stock cultures of primary isolates were prepared by no more than 3–5 passages through PBMCs, and clarified by centrifugation (Sawyer et al., *J Virol*, 1994, 68:1342–1349). They were supplied by Carl Hanson of the California Department of Health Services, Berkeley Calif.

6.3 MT-2 Microplaque Neutralization Assay. The determination of HIV-neutralizing antibody titer employs the preincubation of serially diluted sera or antibody with a fixed amount of HIV followed by infection of HIV-sensitive MT-2 cells and formation of a cell monolayer displaying HIV-induced microplaques. Results are scored by quantitation of the microplaques. The assay is suitable for SI isolates only, whether TCLA or primary isolates, because the microplaques represent giant syncytia formed by MT-2 cells fusing to foci of HIV-infected cells. The assay is appropriate for evaluating inhibition of both virus-to-cell and cell-to-cell transmission because inhibition of syncytia formation results from the action of antibody on either HIV particles or HIV-infected cells, i.e., the assay measures both the inhibition of virus-to-cell HIV-induced fusion or cell-to-cell HIV-induced fusion. Neutralization is then observed by reduction of microplaques as observed by enumeration of propidium iodide-stained plaques 1 week later (See, Hanson et al., *J Clin Microbiol*, 1990, 28:2030–2034). In this assay, both virus and serum or antibody are diluted in 50% pooled, defibrinated normal human plasma to negate any nonspecific enhancing or inhibitory effects.

Results

Candidate CD4- or chemokine coreceptor-derived target antigenic sites and peptides used for immunogenicity and preliminary functional studies are described in Tables 1 and 2. Guinea pigs were immunized as described above with the "b" or "c" forms of the target antigenic site unless noted otherwise in Tables 3 and 4, and immune sera collected at 6 or 8 weeks post initial immunization were analyzed by anti-peptide ELISA and rsCD4 ELISA as described in the Procedures.

As shown in Tables 3 and 4, most of the CD4- and chemokine coreceptor-derived peptide immunogens were highly immunogenic as they evoked anti-peptide antibodies with titers in the range of 2.5 to >5 $Log_{10}$, except for peptides p1590b, p1699b, p1699 c and p1700b. The CD4-derived antigenic sites comprising long segments of the CD4 receptor (e.g., p1612c, p1678b, p1678c, p1686b, p1697b, p1817b, p1889b and 1901b) along with some cyclized target sites were highly crossreactive with rsCD4, as shown by their corresponding >3.5 $Log_{10}$ titers by the anti-rsCD4 ELISA (see Table 3, column A2). Crossreactivity with rsCD4 for each of the peptide constructs was not predictable. Furthermore, such rsCD4 crossreactivity did not extend to corresponding host cell surface CD4 in that among those peptide constructs having high rsCD4 crossreactivity, only p1697b and p1901b were found strongly reactive with CD4 expressing T cells by indirect immunofluorescence staining with HPB-ALL or MT2 cell line cells (Table 3, column B).

In contrast, sera derived from CD4 target antigenic site peptides with a cyclized structure (e.g. p1472b, p1472c) or from the CDR2 domain (e.g., p1403b, p1471c) were highly reactive with the CD4 expressing T cells despite their low crossreactivity with rsCD4 (Table 3, column B). For the chemokine coreceptors, sera derived from peptide constructs p1990, p1999, p2028, p2047, p2048, p2049, p2087 and p2089, mostly with sequences from domains 1, 3 or 4 of the coreceptors, were found reactive with the "surface receptor/coreceptor complex" (Table 4, column B).

The above results indicate that crossreactivity with rsCD4 or surface receptor/coreceptor complex is a complex and unpredictable phenomenon, influenced by conformational features which can only be deduced by experimental observation.

Immune sera (6 or 8 weeks post initial immunization) obtained for the above peptide constructs were also screened for their neutralizing activity against an HIV-1 primary isolate VL 135 of clade B by the MT-2 microplaque neutralization assay as described above. Despite the presence of high titer crossreactive antibodies with rsCD4 or "surface CD4/coreceptor complex" in some of the immune sera, none displayed significant levels of such neutralizing antibodies (Tables 3 and 4, column C).

Immune sera having bright immunofluorescence staining patterns with CD4-expressing T cells were further evaluated for their ability to inhibit or block the binding by MAb B4 to CD4-expressing T cells so as to locate potential effector sites with proximity to discontinuous sites of the conformational epitope recognized by MAb B4. Results obtained from such experiments may lend clues to effective design of new peptide immunogens. This evaluation was accomplished by experiments involving inhibition of immunofluorescence staining of "MAb B4-T cell" binding. CD4+ target T cells (e.g., MT2 T cells) were preincubated with appropriately diluted (e.g., 1:10) immune sera followed by incubation of the cells with biotinylated MAb B4 and FITC-conjugated avidin with detailed procedures described above.

Among all the immune sera evaluated, only sera generated through immunization with peptide p1471c derived from the CD4-CDR2 domain was found to be inhibitory of MAb B4 binding (Table 5). None of those from immunizations with chemokine coreceptor-derived peptides interfered with the "MAb B4-T cell" binding. This lack of "MAb B4-T cell" binding inhibition may relate in part to the less-than-optimal affinity displayed by the antibodies toward the potential effector sites, and may not be due exclusively to the spatial distance of the sites represented by the target antigenic sites to that recognized by MAb B4.

All but one of the hyperimmune sera directed against receptor and coreceptor peptides failed to inhibit MAb B4 binding to T cells, and none displayed neutralizing activity against an HIV primary isolate. Further attempts were made in the design of new peptide constructs with an aim to capture the potential effector sites on the surface CD4 molecule, based on the position of p1471 in the CD4 sequence, the clue provided by the "MAb B4-T cell binding" inhibition study.

More specifically, peptides comprising target antigenic sites surrounding the CD4-CDR2 domain spanning amino acid residues from 20 to 75 according to the numbering system of SEQ ID NO:1 were revisited and additional peptide constructs covering this region were redesigned with a particular emphasis on the preservation of the 3D-structure of this region by insertion of cysteine residues at both N- and C-termini of peptides derived from this CDR2 region with a loop size in the range of 30 to 45 amino acids. Amino acid sequences for representative peptide constructs derived from this region are shown in Table 6.

Immune sera were collected at 6 or 8 weeks post initial immunization and evaluated similarly to those described in the previous screening. Among the 41 target antigenic sites evaluated, p2057, p2189, p2190, and p2240 (SEQ ID NOS:4, 11, 10, and 5), as "c" constructs (SEQ ID NOS:32–35), were found to elicit neutralizing antibodies directed against primary HIV-1 isolates (Table 6). Isolate VL135 (Table 6) (Sawyer et al., *J. Virol.,* 1994, 68:1342–1349) is a representative neutralization-resistant primary isolate. It is not an atypical neutralization-sensitive primary isolate that can be used to provide apparent but misleading positive (D. Burton and J. Moore, *Nature Medicine,* 1998, 4:495–48). Therefore, the viral neutralization observed here is not inactivation of an easily neutralized virus, but is evidence for protective immunity from challenge by a field isolate of HIV. There have been no prior observations in the field of AIDS research where chemically defined immunogens elicited antibodies with this critical HIV neutralization function. Despite the lack of binding activity by MAb B4 to any of the CD4-CDR2 domain site peptides (as shown in copending patent application published as WO 97/46697), a CD4-CDR2 target site is demonstrated here to be proximal to the scattered discontinuous epitope that constitutes the recognition site for neutralizing monoclonal antibody B4. This recognition site appears to contain peptide sites from all four domains of CD4 probably due to the curved nature of the "surface receptor/coreceptor complex comprising CD4", recognized by MAb B4. This "surface CD4" is distinct from the well-known extended 3D-model of rsCD4. It is worth noting that only certain target antigenic sites derived from the CD4-CDR2 region, i.e., those spanning a more extended area and presented as cyclic peptides (e.g., p2057c, p2189c, p2190c and p2240c, SEQ ID NOS:32–35), elicited such neutralizing antibodies.

Example 2

Hyperimmune Sera Generated by Peptides p2057c and p2240c Demonstrate Broadly Reactive Neutralizing Antibodies Against Primary Hiv of Multiple Clades As shown in Table 7, hyperimmune sera derived from bleeds obtained 15 and 12 weeks post initial immunization for peptide immunogens p2057c and p2240c (SEQ ID NOS:32 and 35) both demonstrated significant 90% neutralizing antibody titers against HIV primary isolates of multiple clades in a pattern parallel to that demonstrated by MAb B4. The neutralizing antibody titers ranged in an increasing order from 1:20 to 1:185 for primary isolates of clade D, A, B(DH12), E, to B(VL 135) and clade C for immune sera to p2057c (SEQ ID NO:32); from 1:20 to 1:324 for primary isolates of clades D, B(DH12), A, E to clade B (VL 135) for immune sera to p2240c (SEQ ID NO:35). For the purpose of determining equivalence, the neutralization activity of MAb B4 ranged from 25.6 μg/ml to 1.54 μg/ml for HIV-1 primary isolates of clades D, A, E, C, B(DH12), to clade B (primary isolate VL 135). In comparison, guinea pig sera directed at the N-terminal gp 120 V3 domain and monoclonal antibodies directed either at the gp120N-terminal V3 domain of HIV-1 MN (MAb 50.1) or a less variable conformational gp120CD4 binding site (MAb IgG1 b12) failed to neutralize any of these neutralization-resistant HIV primary isolates. Dilutions of 1:20 to 1:300 of the anti-p2057c and anti-p2240c immune sera which provide for 90% neutralization of primary isolates of HIV of clades A to E, as demonstrated in Table 7, would approximate a MAb B4 concentration in undiluted serum of about 300 μg/ml from a calculation of MAb B4 concentration and serum dilutions at equivalent neutralization activities (i.e., an average of the MAb B4 concentration (μg/ml)×immune serum dilution factor for neutralizing activity against each of the corresponding isolates).

Example 3

Correlation of Neutralizing Antibody Titers In Sera with Protective Efficacy in Rhesus Macaques Against SIVmac251 Infection In copending patent application WO 97/46697, the protective efficacy of MAb B4 and its correlation to in vitro neutralizing antibody titers was evaluated by a challenge trial of MAb B4 against the experimental infection of rhesus macaques with SIV, a commonly used animal model for human AIDS.

In that study, rhesus macaques were infused with MAb B4 and sera were collected at pre-treatment, pre-challenge, and 1 hr post-challenge time points for evaluation. The serum level of the MAb B4 antibody, determined by rsCD4 immunoassay against a precalibrated MAb B4 curve, was found to be in the range of 30–45 μg/ml for all animals receiving a dosage of 5 mg/kg body weight. Three out of four animals receiving this amount of MAb B4 were protected against $SIV_{mac251}$, for the one year period monitored. The level (i.e., 30–45 μg/ml) of serum MAb B4 present in the challenged animals is far lower than the estimated level of anti-(CD4-CDR2 antigen peptide) antibody (around 300 μg/ml) that would have been present in the immune sera generated in the hosts had they been immunized with an immunogenic composition comprising p2057c or p2240c (SEQ ID NOS:32 and 35).

Therefore, hosts immunized with a peptide composition of the present invention comprising SEQ ID NOS:4,5,10 and 11 or homologs thereof can be predicted to have protective immunity from HIV infection by primary HIV isolates of multiple clades.

Example 4

Immunogenic Peptide Compositions Comprising a Promiscuous Artificial Th Epitope

An artificial Th/CD4-CDR2 antigen peptide was synthesized of the design (SEQ ID NO:6)-Gly-Gly-(SEQ ID NO:5) and given the designation SEQ ID NO:60.

The peptide of SEQ ID NO:60 was formulated in ISA 206/DDA. ISA 206/DDA is an oil/water emulsion in which Dimethydioctadecylammonium bromide (DDA) is dispersed into MONTANIDE™ ISA 206 at 30 mg/ml (MONTANIDE™ ISA 206 is an oily metabolizable solution supplied by SEPPIC Inc. of Fairfield, N.J.). The oil suspension is then emulsified at a 1:1 volume ratio into an aqueous peptide solution which has been adjusted for peptide content so as to provide the desired dose of peptide composition in 0.5 ml of the final preparation.

The immunogenicity of SEQ ID NO:60 in the above formulation was established in guinea pigs who received 100 µg/dose, given at weeks 0, 3, and 6. Immunogenicity was determined by anti-peptide ELISA as described in Example 1 using SEQ ID NO:5 as the cyclized target antigenic site peptide used for the solid-phase substrate. Six of six guinea pigs were successfully seroconverted to ELISA reactivity.

Significantly, SEQ ID NO:60 was also found to be highly immunogenic and of functional activity in a large animal. An immunogenic composition comprising SEQ ID NO:60 was formulated in Incomplete Freunds Adjuvant (IFA), 300 µg/dose, and administered to a swine by intramuscular injection on weeks 0, 3, and 6. The swine seroconverted and the serum from week 8 was tested for neutralization activity against primary isolate HIV-1 VL135 by the MT-2 Microplaque Neutralization Assay (Example 1). The swine serum sample provided 50% neutralization of input virus at a dilution of 1:249, and 90% neutralization at a dilution of 1:97. Therefore, immunization with a peptide composition of the invention imparted a large animal host with an immune response that included antibody to the host cell receptor comprising CD4 and neutralizing activity toward HIV.

TABLE 1

Structural Description of CD4-Derived Peptides

| Code | Description | Form† | Code | Description | Form† |
|---|---|---|---|---|---|
| — | rsCD4 | a | p1616 | (C)CD4 (40–43)(C)* | b, c |
| p1403 | CD4 (43–55) | b, c | p1617 | (C)CD4 (52–54)(C)* | b, c |
| p1404 | (C)CD4 (38–47)(C)* | b, c | p1618 | (C)CD4 (51–55)(C)* | b, c |
| p1405 | CD4 (81–92) | b, c | p1619 | (C)CD4 (48–52)(C)* | b, c |
| p1406 | CD4 (18–29) | b, c | p1620 | (C)CD4 (85–90)(C)* | b, c |
| p1460 | CD4 (1–109) | a | p1621 | (C)CD4 (85–89)(C)* | b, c |
| p1468 | CD4 (47–64) | b, c | p1622 | (C)CD4 (85–90)(C)* | b, c |
| p1469 | CD4 (39–45) | b, c | p1678 | (C)CD4 (291–306)(C)* | b, c |
| p1470 | (C)CD4 (36–45)(C)* | b, c | p1679 | (C)CD4 (297–302)(C)* | b, c |
| p1471 | CD4 (39–67) | b, c | p1680 | (C)CD4 (303–315)(C)* | b, c |
| p1472 | (C)CD4 (115–130(C → S)–137) | b, c | p1681 | (C)CD4 (309–313)(C)* | b, c |
| p1518 | CD4 (60–109) | b, c | p1682 | (C)CD4 (314–328)(C)* | b, c |
| p1585 | (C)CD4 (36–47)(C)* | b, c | p1683 | (C)CD4 (291–306)(C)* | b, c |
| p1586 | (C)CD4 (42–59)(C)* | b, c | p1684 | (C)CD4 (315–346)(C)* | b, c |
| p1587 | (C)CD4 (44–56)(C)* | b, c | p1685 | (C)CD4 (338–343)(C)* | b, c |
| p1588 | (C)CD4 (46–55)(C)* | b, c | p1686 | (C)CD4 (341–360)(C)* | b, c |
| p1589 | (C)CD4 (79–96)(C)* | b, c | p1687 | (C)CD4 (349–353)(C)* | b, c |
| p1590 | (C)CD4 (104–115)(C)* | b, c | p1688 | (C)CD4 (202–205)(C)* | b, c |
| p1608 | CD4 (16–25)(C)* | c | p1689 | (C)CD4 (213–226)(C)* | b, c |
| p1609 | (C)CD4 (118–128)(C)* | c | p1690 | (C)CD4 (217–221)(C)* | b, c |
| p1610 | (C)CD4 (127–130(C → S)–141)(C)* | c | p1691 | (C)CD4 (228–239)(C)* | b, c |
| p1611 | (C)CD4 (138–146)(C)* | c | p1692 | (C)CD4 (231–237)(C)* | b, c |
| p1612 | (C)CD4 (133–153)(C)* | c | p1693 | (C)CD4 (235–251)(C)* | b, c |
| p1613 | CD4 (159–169)(C)* | c | p1694 | (C)CD4 (243–246)(C)* | b, c |
| p1615 | (C)CD4 (39–44)(C)* | b, c | p1695 | (C)CD4 (247–259)(C)* | b, c |
| p1696 | (C)CD4 (250–255)(C)* | b, c | p1817 | CD4 [118–130(C)–159(C)–165]* | b |
| p1697 | (C)CD4 (274–286)(C)* | b, c | p1818 | CD4 (81–92)) × CD4 (6–20) | b x a |
| p1698 | (C)CD4 (277–282)(C)* | b, c | p1820 | CD4 (154–165) × CD4 (117–140) | a x b |
| p1699 | CD4 (168–182) | b, c | p1821 | CD4 (154–165) × CD4 (123–134) | a x b |
| p1700 | (C)CD4 (151–178)(C)* | b, c | p1848 | CD4 [(68–92) - M] | g |
| p1701 | CD4 (361–375) | b, c | p1856 | CD4 (79–88) × CD4 (1–20) | a x b |
| p1702 | CD4 (14–22) | b | p1857 | CD4 (79–88) × CD4 (1–20) | b x a |
| p1761 | CD4 (123–134) | b | p1858 | CD4 (1–20) | b |
| p1763 | CD4 (72–92) | b | p1864 | CD4 (1–20)) × CD4 (156–173) | b x a |
| p1765 | (C)CD4 (70–84) | b | p1868 | CD4 (297–351)* | b |
| p1766 | CD4 (6–26) | b | p1875 | CD4 (87–98) | b |
| p1767 | CD4 (6–20) | b | p1876 | CD4 (81–98) | b |
| p1768 | CD4 (154–165) | b | p1877 | CD4 (76–98) | b |
| p1769 | CD4 (156–173) | b | p1878 | (C)CD4 (77–98)(C)* | b |
| p1770 | CD4 (146–170) | b | p1879 | (C)CD4 (77–103)* | b |
| p1771 | CD4 (117–140) | b | p1880 | CD4 (72–103)* | b |
| p1773 | CD4 (72–92) × CD4 (6–26) | a x b | p1886 | CD4 (341–375) | b |
| p1775 | CD4 (72–92) × CD4 (6–20) | a x b | p1889 | CD4 (213–251) | b |
| p1777 | CD4 (117–140)) × CD4 (154–165) | a x b | p1901 | CD4 (1–26) | b |
| p1778 | CD4 (117–140)) × CD4 (156–173) | a x b | p1905 | CD4 (303–C345–353)* | b |
| p1780 | CD4 (123–134)) × CD4 (154–165) | a x b | p2037 | (C)CD4 (68–C84–88)* | b |
| p1781 | CD4 (123–134)) × CD4 (154–173) | a x b | p2038 | (C)CD4 (68–C84)* | b |

TABLE 1-continued

Structural Description of CD4-Derived Peptides

| Code | Description | Form† | Code | Description | Form† |
|---|---|---|---|---|---|
| p1783 | CD4 (6–20) × CD4 (72–92) | a x b | p2078 | CD4 (1–20) | e |
| p1784 | CD4 (6–26) × CD4 (72–92) | a x b | p2100 | (C)CD4 (68–C84–92)* | b |
| p1813 | CD4 (79–88) | b | p2101 | (C)CD4 (68–C84–98)* | b |

† Form of peptide constructs is designated as a, b, c, e, g, and x, where:
a represents Target Antigenic Site
b represents HBsTh-GG-Target Antigenic Site
c represents Inv-GG-HBsTh-GG-Target Antigenic Site
e represents Target Antigenic Site -GG-HBsTh
g represents branched tetramer of Target Antigenic Site on $K_2KAA$ core
x represents crosslinkage of peptide chains through an interchain disulfide bond
*Peptide is cyclized through cysteines at or near N and C termini of Target Antigenic Site

TABLE 2

Structural Description of Peptides Derived from β Chemokine Receptors

Peptide Antigens Representing Chemokine Receptor External Domain

| Type of Chemokine Receptor | 1 | | | 2 | | | 3 | | | 4 | | | 2/3 | | |
|---|---|---|---|---|---|---|---|---|---|---|---|---|---|---|---|
| | Code | Description | Form | Code | Description | † | Code | Description | † | Code | Description | † | Code | Description | † |
| CC-CKR1# | p1999 | AA1–AA34 | e | p2004 | AA94–AA107 | e | p2027 | AA168–AA203 | b | p2028 | AA261–AA287 | b | p2006 | AA94–AA107 × AA172–AA203 | d x a |
| CC-CKR2# | p2086 | AA1–AA43 | e | p2087 | AA100–AA114 | b | p2088 | AA182–AA207 | b | p2089 | AA269–AA285 | b | p2091 | AA100–AA114 × AA182–AA207 | b x a |
| CC-CKR3# | p2079 | AA1–AA35 | e | p2080 | AA92–AA107 | b | p2081 | AA173–AA204 | b | p2082 | AA265–AA281 | b | p2084 | AA92–AA107 × AA173–AA204 | b x a |
| CC-CKR5# | p2045 | AA1–AA29 | e | p2046 | AA88–AA102 | b | p2047 | AA168–AA199 | b | p2048 | AA261–AA277 | b | p2049 | AA88–AA102 × AA168–AA199 | a x a |
| Fusin (LESTR)# | p1987 | AA1–AA38 | e | p2041 | AA103–AA114 | b | p1990 | AA181–AA203 | e | p1991 | AA262–AA285 | b | p1996 | AA181–203 × AA106–AA111 | d x a |

† Forms of peptide constructs are listed as a, b, d, e, and x, where:
a represents Target Antigenic Site
b represents HBsTh-GG-Target Antigenic Site
d represents CT P11 Th-GG-HBsTh-GG-Target Antigenic Site
e represents Target Antigenic Site -GG-HBsTh
x represents crosslinkage of two peptide chains through an interchain disulfide bond
Chemokine receptor external domain peptides, numbering system of the amino acid sequences deduced from nucleic acid sequences in:
LESTR (Loetscher et al, J Biol. Chem. 1994, 269:232)
CC-CKR1, CC-CKR2b, CC-CKR3, CC-CKR5 (M. Samson et al, Biochemistry 1996, 35, 3362)

TABLE 3

Immunogenicity and Functional Mapping of CD4-Derived Peptides by ELISA and Neutralization Assays

| Peptide code | A1 | A2 | B | C | Pept

TABLE 3-continued

Immunogenicity and Functional Mapping of CD4-Derived Peptides by ELISA and Neutralization Assays

| Peptide code | A1 | A2 | B | C | Peptide code | A1 | A2 | B | C | Peptide code | A1 | A2 | B | C |
|---|---|---|---|---|---|---|---|---|---|---|---|---|---|---|
| p1405 c | >5 | 1.8 | – | <1:10 | p1608 c | 3.3 | 0.8 | tr | <1:10 | p1680 b | 4.5 | 2.9 | ++ | <1:10 |
| p1406 b | 4.3 | 0.9 | – | 1:12 | p1609 c | 4.3 | 1.5 | tr | <1:10 | p1680 c | 4.5 | 2.5 | ++ | <1:10 |
| p1406 c | 4.3 | 0.9 | – | <1:10 | p1610 c | 3.3 | <1 | – | <1:10 | p1681 b | 4.3 | 1.8 | ++ | <1:10 |
| p1460 a | 4.3 | 2.4 | – | <1:10 | p1611 c | 2 | 1.9 | tr | <1:10 | p1681 c | 3.5 | 1.6 | + | <1:10 |
| p1460 # | 3.3 | 1.2 | – | <1:10 | p1612 c | >5 | >5 | – | <1:10 | p1682 b | >5 | 2.7 | + | <1:10 |
| p1469 b | 4.3 | 2.6 | – | <1:10 | p1613 c | 4.3 | 1.0 | tr | <1:10 | p1682 c | >5 | 2.7 | + | <1:10 |
| p1469 c | 4.3 | 3.1 | tr | <1:10 | p1614 b | >5 | 1.9 | – | <1:10 | p1683 b | >5 | 1.8 | + | <1:10 |
| p1470 b | 3 | 0.5 | tr | <1:10 | p1614 c | >5 | 2.6 | – | <1:10 | p1683 c | 4.0 | 1.6 | + | <1:10 |
| p1471 a | 3.3 | 2.5 | – | <1:10 | p1615 b | 2.0 | 1.3 | – | <1:10 | p1684 b | >5 | 2.9 | + | <1:10 |
| p1471 b | 3.3 | 2.8 | tr | <1:10 | p1615 c | 4.3 | 1.7 | – | <1:10 | p1684 c | >5 | 2.5 | ++ | <1:10 |
| p1471 c | 4.3 | 2.7 | ++ | <1:10 | p1616 b | >5 | 1.1 | tr | <1:10 | p1685 b | >5 | 1.8 | + | <1:10 |
| p1472 b | 4.3 | 1.3 | +++ | <1:10 | p1616 c | 3.8 | 1.2 | – | <1:10 | p1685 c | 3.0 | 1.6 | + | <1:10 |
| p1472 c | 4.3 | 1.8 | +++ | <1:10 | p1617 b | >5 | 1.2 | – | <1:10 | p1686 b | 4.3 | 4.1 | + | <1:10 |
| p1518 b | 4.3 | 3.7 | – | <1:10 | p1617 c | 2.0 | 1.4 | – | <1:10 | p1686 c | 4.3 | 3.5 | tr | <1:10 |
| p1518 c | 4.3 | 3.7 | – | <1:10 | p1618 b | >5 | 1.0 | – | <1:10 | p1687 b | 4.3 | 2.9 | ++ | <1:10 |
| p1585 b | 4.3 | 3.0 | – | <1:10 | p1618 c | 4.3 | 1.1 | – | <1:10 | p1687 c | 4.3 | 2.0 | + | <1:10 |
| p1585 c | 4.3 | 3.0 | – | <1:10 | p1619 b | 4.3 | 1.4 | – | <1:10 | p1688 b | >5 | 2.4 | + | <1:10 |
| p1586 b | 4.3 | 3.2 | – | <1:10 | p1619 c | 4.3 | 1.4 | – | <1:10 | p1688 c | 4.3 | 2.4 | + | <1:10 |
| p1586 c | 4.3 | 3.2 | – | <1:10 | p1620 b | >5 | 1.7 | tr | <1:10 | p1689 b | 4.3 | 2.9 | ++ | <1:10 |
| p1587 b | 4.3 | 3.2 | – | <1:10 | p1620 c | >5 | 1.4 | – | <1:10 | p1689 c | 3.8 | 2.5 | ++ | <1:10 |
| p1587 c | 4.3 | 3.2 | – | <1:10 | p1621 b | >5 | 1.4 | – | <1:10 | p1690 b | 3 | 2.1 | ++ | <1:10 |

| Peptide code | A1 | A2 | B | C | Peptide code | A1 | A2 | B | C |
|---|---|---|---|---|---|---|---|---|---|
| p1690 c | 2.0 | 1.9 | ++ | <1:10 | p1771 b | >5 | 2.8 | +++ | <1:10 |
| p1692 b | 4.3 | 1.7 | + | <1:10 | p1773 x | >5 | 1.2 | – | <1:10 |
| p1693 c | 4.3 | 2.7 | + | <1:10 | p1775 x | 4.3 | 1.3 | – | <1:10 |
| p1694 b | 3.0 | 1.8 | – | <1:10 | p1777 x | 4.5 | 1.7 | – | <1:10 |
| p1694 c | 3 | 1.8 | tr | <1:10 | p1778 x | >5 | 2.7 | – | <1:10 |
| p1695 b | 3.0 | 2.0 | ++ | <1:10 | p1780 x | >5 | 1.2 | ++ | <1:10 |
| p1695 c | 2.5 | 2.1 | + | <1:10 | p1781 x | >5 | 2.7 | – | <1:10 |
| p1696 b | >5 | 1.8 | + | <1:10 | p1783 x | 4.3 | 1.2 | – | <1:10 |
| p1696 c | >5 | 1.9 | tr | <1:10 | p1784 x | 4.3 | 1.4 | – | <1:10 |
| p1697 b | >5 | 4.2 | ++ | <1:10 | p1813 b | 3.3 | 1.5 | – | <1:10 |
| p1697 c | 3.5 | 2.1 | + | <1:10 | p1817 b | >5 | 4.5 | + | <1:10 |
| p1697 c | 3.5 | 2.1 | ++ | <1:10 | p1818 x | >5 | 1.3 | – | <1:10 |
| p1698 b | 3.5 | 1.7 | – | <1:10 | p1820 x | >5 | 2.5 | tr | <1:10 |
| p1698 c | 2.0 | 1.8 | – | <1:10 | p1821 x | >5 | 1.3 | – | <1:10 |
| p1699 b | 1.5 | – | – | <1:10 | p1848 g | >5 | 3.1 | +++ | <1:10 |
| p1699 c | 1.5 | – | – | <1:10 | p1856 x | 4.3 | 1.5 | – | <1:10 |
| p1700 b | 1.5 | – | – | <1:10 | p1857 x | >5 | 2.3 | – | <1:10 |
| p1700 c | 2.5 | 1.7 | – | <1:10 | p1864 x | 3 | 2.5 | +++ | <1:10 |
| p1701 b | >5 | 2.2 | ++ | <1:10 | p1878 b | 4 | 2 | – | <1:10 |
| p1701 c | >5 | 2.6 | ++ | <1:10 | p1889 b | >5 | 4.4 | 1.5 | <1:10 |
| p1761 b | 4.3 | 2.2 | ++ | <1:10 | p1901 b | >5 | 4 | 3 | <1:10 |
| p1763 b | 4.3 | 2.1 | – | <1:10 | p2037 b | >5 | NT | tr | <1:10 |
| p1765 x | 3.5 | 1.3 | – | <1:10 | p2038 b | 4.3 | NT | – | <1:10 |
| p1766 b | >5 | 1.2 | – | <1:10 | p2078 b | 4.3 | NT | ++ | <1:10 |
| p1767 b | 3.8 | 3.0 | – | <1:10 | p2100 b | 3.5 | NT | + | <1:10 |
| p1768 b | >5 | 1.4 | – | <1:10 | p2101 b | 3.0 | NT | tr | <1:10 |
| p1769 b | >5 | 1.3 | – | <1:10 | | | | | |

Legend, Table 3:
: p1460 - BSA Conjugate
A1: $Log_{10}$ ELISA anti-target antigenic site reciprocal titer
A2: $Log_{10}$ ELISA anti-rsCD4 reciprocal titer
B: IFA (Indirect Immunofluorescence Staining Assay)
C: Serum dilution giving 50% inhibition in MT-2 Neutralization Assay on Clade B HIV-1 VL 135
g: Branched tetrameric peptide
tr: trace
NT: not determined

TABLE 4

Immunogenicity and Functional Mapping by ELISA and Neutralization Assays of Chemokine Coreceptor-Derived Peptides

| Type of Chemokine Receptor | Peptide Antigen Representing the Respective Chemokine Receptor Domain | | | | | | | | | | | | | | | | | | | |
|---|---|---|---|---|---|---|---|---|---|---|---|---|---|---|---|---|---|---|---|---|
| | 1 | | | | 2 | | | | 3 | | | | 4 | | | | 2/3 | | | |
| | Code | A | B | C | Code | A | B | C | Code | A | B | C | Code | A | B | C | Code | A | B | C |
| CC-CKR1 | p1999 | >5 | +++ | <1:10 | p2004 | >5 | – | <1:10 | p2027 | 2.5 | – | <1:10 | p2028 | 4.3 | ++ | <1:10 | p2006 | >5 | – | <1:10 |
| CC-CKR2 | p2086 | 4.3 | – | <1:10 | p2087 b | 4.3 | ++ | <1:10 | p2088 | >5 | – | <1:10 | p2089 | 4.3 | + | <1:10 | p2091 | 3.5 | – | <1:10 |
| CC-CKR3 | p2079 | 4.3 | tr | <1:10 | p2080 b | 3.0 | – | <1:10 | p2081 | 3.0 | – | <1:10 | p2082 | 2.5 | tr | <1:10 | p2084 | 4.3 | tr | <1:10 |

TABLE 4-continued

Immunogenicity and Functional Mapping by ELISA and Neutralization Assays of Chemokine Coreceptor-Derived Peptides

| Type of Chemokine Receptor | Peptide Antigen Representing the Respective Chemokine Receptor Domain | | | | | | | | | | | | | | | | | | | |
|---|---|---|---|---|---|---|---|---|---|---|---|---|---|---|---|---|---|---|---|---|
| | 1 | | | 2 | | | | 3 | | | | 4 | | | | 2/3 | | | |
| | Code | A | B | C | Code | A | B | C | Code | A | B | C | Code | A | B | C | Code | A | B | C |
| CC-CKR5 | p2045 | >5 | tr | <1:10 | p2046 b | 3.0 | tr | <1:10 | p2047 | 3.5 | ++ | <1:10 | p2048 | 4.8 | ++++ | <1:10 | p2049 | 4.3 | ++ | <1:10 |
| Fusin (LESTR) | p1987 | >4 | tr | <1:10 | p2041 b | 4.3 | – | <1:10 | p1990 | 2.5 | ++ | <1:10 | p1991 | 3.5 | – | <1:10 | p1996 | >5 | – | <1:10 |

A: $Log_{10}$ ELISA anti-target antigenic site reciprocal titer
B: IFA (Indirect Immunofluorescence Staining Assay)
C: Serum dilution giving 50% inhibition in MT-2 Neutralization Assay on Clade B HIV-1 VL 135
tr: trace

TABLE 5

INHIBITION OF MAB B4 BINDING TO MT2 T CELLS BY IMMUNE SERA GENERATED BY CD4- OR CHEMOKINE CORECEPTOR-DERIVED PEPTIDES

| | CD4-derived peptide | | | | | Chemokine coreceptor-derived peptide | | | | |
|---|---|---|---|---|---|---|---|---|---|---|
| Peptide code* | Immune sera (1:50)† FITC-Gt αGP IgG | | Immune sera (1:10)# B4-Biotin × Avidin-FITC | | | Peptide code* | Immune sera (1:50)† FITC-Gt αGP IgG | | Immune sera (1:10)# B4-Biotin × Avidin-FITC | | |
| | % Pos cells | Intensity | % Pos cells | Intensity | Inhibition | | % Pos cells | Intensity | % Pos cells | Intensity | Inhibition |
| 1430b | >95 | +++ | >95 | +++ | No | 1990e | >95 | ++ | >95 | ++ | No |
| 1471c | >95 | +++ | 0 | 0 | Yes | 1999e | >95 | ++ | >95 | ++ | No |
| 1472c | >95 | +++ | >95 | ++ | No | 2028b | >95 | ++ | >95 | ++ | No |
| 1684c | >95 | +++ | >95 | ++ | No | 2047b | >95 | ++ | >95 | ++ | No |
| 1771b | >95 | ++ | >95 | ++ | No | 2048b | >95 | +++ | >95 | ++ | No |
| 1817b | >95 | + | >95 | ++ | No | 2049x | >95 | ++ | >95 | ++ | No |
| 1848d | >95 | +++ | >95 | ++ | No | 2087b | >95 | ++ | >95 | ++ | No |
| 1864 | >95 | +++ | >95 | ++ | No | rsCD4 | >95 | +++ | >95 | ++ | No |
| 1889b | >95 | +++ | >95 | ++ | No | MAb B4 | >95 | +++ | 0 | 0 | Yes |
| 1901b | >95 | +++ | >95 | ++ | No | Control‡ | — | – | >95 | ++ | No |

† IFA
inhibitory IFA
*see legend to Table 2 for description of peptide codes
‡ medium alone

TABLE 6

Ability of Peptides to Elicit Neutralizing Antibodies Against HIV Primary Isolate

| Peptide Code | Description of Target Antigenic Site | Amino Acid Sequence of Target Antigenic Peptide (a) | Form | A1 | A2 | B | C |
|---|---|---|---|---|---|---|---|
| p1403 | CD4 (43–55) (SEQ ID NO: 14) | FLTKGPSKLNDRA | b | 4.3 | 2.6 | ++ | <1:10 |
| | | | c | 4.3 | 2.1 | tr | <1:10 |
| p1404 | (C)CD4 (38–47)(C)* (SEQ ID NO: 15) | (C)GNQGSFLTKG(C) | b | 2 | <1 | tr | NT |
| | | | c | 4.3 | 2.6 | ++ | <1:10 |
| p1468 | CD4 (49–63) (SEQ ID NO: 16) | GPSKLNDRADSRRSLWDQ | b | 4.3 | 3.1 | tr | <1:10 |
| | | | c | 4.3 | 2.4 | – | <1:10 |
| p1469 | CD4 (39–45) (SEQ ID NO: 17) | NQGSFLT | b | 4.3 | 2.6 | – | <1:10 |
| | | | c | 4.3 | 3.1 | tr | <1:10 |
| p1470 | CD4 (37–46)* (SEQ ID NO: 18) | (C)ILGNQGSFLT(C) | b | 3 | 0.5 | tr | <1:10 |
| | | | c | 1.5 | 0.8 | – | <1:10 |
| p1471 | CD4 (39–67) (SEQ ID NO: 19) | NQGSFLTKGPSKLNDRADSRRSLWDQGNF | b | 3.3 | 2.8 | tr | <1:1 |
| | | | c | 4.3 | 2.7 | – | <1:10 |
| p1518 | CD4 (60–109) (SEQ ID NO: 20) | SKLNDRADSRRSLWDQGNFPLIIKNLKIEDSDTYICEVED QKEEVQLLVFGLTANSDTHLL | b | 4.3 | 3.7 | – | <1:10 |
| | | | c | 4.3 | 3.7 | – | <1:10 |
| p1585 | CD4 (36–47)* (SEQ ID NO: 21) | (C)ILGNQGSFLTKG(C) | b | 4.3 | 3.0 | – | <1:10 |
| | | | c | 4.3 | 3.0 | – | <1:10 |
| p1586 | CD4 (42–59)* (SEQ ID NO: 22) | (C)SFLTKGPSKLNDRADSRR(C) | b | 4.3 | 3.2 | – | <1:10 |
| | | | c | 4.3 | 3.2 | – | <1:10 |
| p1587 | CD4 (44–56)* (SEQ ID NO: 23) | (C)LTKGPSKLNDRAD(C) | b | 4.3 | 3.2 | – | <1:10 |
| | | | c | 4.3 | 3.2 | – | <1:10 |
| p1588 | CD4 (46–55)* (SEQ ID NO: 24) | (C)KGPSKLNDRA(C) | b | 4.3 | 3.2 | – | <1:10 |
| | | | c | 4.3 | 3.2 | – | <1:10 |
| p1589 | CD4 (79–96)* (SEQ ID NO: 25) | (C)SDTYICEVEDQKEEVQLL(C) | b | 4.3 | 2.2 | – | <1:10 |
| | | | c | 4.3 | 2.2 | – | <1:10 |

TABLE 6-continued

Ability of Peptides to Elicit Neutralizing Antibodies Against HIV Primary Isolate

| Peptide Code | Description of Target Antigenic Site | Amino Acid Sequence of Target Antigenic Peptide (a) | Form | A1 | A2 | B | C |
|---|---|---|---|---|---|---|---|
| p1614 | CD4 (38–45)(C)* (SEQ ID NO: 26) | (C)GNQGSFLT(C) | b | >5 | 1.9 | NT | <1:10 |
|  |  |  | c | >5 | 2.6 | NT | <1:10 |
| p1615 | CD4 (39–44)(C)* (SEQ ID NO: 27) | (C)NQGSFL(C) | b | 2.0 | 1.3 | NT | <1:10 |
|  |  |  | c | >4 | 1.7 | NT | <1:10 |
| p1616 | CD4 (40–43)(C)* (SEQ ID NO: 28) | (C)QGSF(C) | b | >5 | 1.1 | NT | <1:10 |
|  |  |  | c | 3.5 | 1.2 | NT | <1:10 |
| p1617 | CD4 (52–54)(C)* (SEQ ID NO: 29) | (C)NTR(C) | b | >5 | 1.2 | NT | <1:10 |
|  |  |  | c | 2.9 | 1.4 | NT | <1:10 |
| p1618 | CD4 (51–55)(C)* (SEQ ID NO: 30) | (C)LNTRA(C) | b | >5 | 1.0 | NT | <1:10 |
|  |  |  | c | >4 | 1.1 | NT | <1:10 |
| p1619 | CD4 (48–52)(C)* (SEQ ID NO: 31) | (C)PSKLN(C) | b | >4 | 1.4 | NT | <1:10 |
|  |  |  | c | >4 | 1.4 | NT | <1:10 |
| p2057 | (C)CD4 (27–66)(C)* (SEQ ID NO: 4) | (C)HWKNSNQIKILGNQGSFLTKGPSKLNTRADSRRSLWDQGN(C) | b | >5 | 4.4 | NT | <1:10 |
|  |  |  | c | 4.5 | >5 | NT | 1:165 |
| p2189 | (C)CD4 (39–71)* [$F_{67} \rightarrow C$] (SEQ ID NO: 11) | (C)NQGSFLTKGPSKLNDRADSRRSLWDQGN(C)PLII | c | >5 | >5 | +++ | 1:23 |
| p2190 | (C)CD4 (27–71)* [$F_{67} \rightarrow C$] (SEQ ID NO: 10) | (C)HWKNSNQIKILGNQGSFLTKGPSKLNDRADSRRSLWDQGN(C)PLII | c | >5 | >5 | +++ | 1:15 |
| p2240 | (C)CD4 (39–66)(C)* (SEQ ID NO: 5) | (C)NQGSFLTKGPSKLNDRADSRRSLWDQGN(C) | c | >4 | >5 | +++ | 1:283 |

A1: $Log_{10}$ ELISA anti-target antigenic site reciprocal titer
B: IFA
A2: $Log_{10}$ ELISA anti-rsCD4 reciprocal titer
C: Serum dilution giving 50% inhibition in MT-2 Neutralization Assay on Clade B HIV-1 VL 135
*: cyclized peptides

TABLE 7

Neutralization of HIV-1 Primary Isolates of Clades A, B, C, D and E by Monoclonal Antibodies and Immune Sera (MT-2 Microplaque Neutralization Assay)

| Type of Antibodies | UGO29# (Clade A) 90% | VL 135 (Clade B) 90% | ZIM 748# (Clade C) 90% | UG266# (Clade D) 90% | TH036# (Clade E) 90% | DH12# (Clade B) 90% |
|---|---|---|---|---|---|---|
| α p2057c (SEQ ID NO: 32) (15 wpi) | 1:20 | 1:157 | 1:184 | 1:20 | 1:87 | 1:20 |
| α p2240c (SEQ ID NO: 35) (12 wpi) | 1:76 | 1:324 | NT | 1:20 | 1:102 | 1:36 |
| MAb B4 | 6.76 μg/ml | 1.54 μg/ml | 2.82 μg/ml | 25.6 μg/ml | 3.32 μg/ml | 2.1 μg/ml |
| α N-terminal $V3_{MN}$ | >100 μg/ml | >100 μg/ml | >100 μg/ml | >100 μg/ml | >100 μg/ml | >100 μg/ml |
| Ig G1 b12 MAb α gp120 | 38.5 μg/ml | 41.7 μg/ml | >50 μg/ml | >50 μg/ml | >50 μg/ml | NT |
| MAb 50.1 α gp120 (N-terminal V3) | >50 μg/ml | >50 μg/ml | >50 μg/ml | >50 μg/ml | >50 μg/ml | >50 μg/ml |

: HIV-1 primary isolates provided by WHO Global Program on AIDS.

TABLE 8

AMINO ACID SEQUENCES OF FOREIGN PATHOGEN-DERIVED TH EPITOPES

| Description of Th | SEQ ID NO: | Amino Acid Sequences |
|---|---|---|
| $MV_{F288-302}$ Th | 38 | LSEIKGVIVHRLEGV |
| $MV_{F258-277}$ Th | 39 | GILESRGIKARITHVDTESY |
| $TT_{830-844}$ Th | 40 | KKQYIKANSKFIGITEL |
| $TT_{947-966}$ Th | 41 | KKFNNFTVSFWLRVPKVSASHL |
| $PT_{149-176}$ Th | 42 | KKLRRLLYMIYMSGLAVRVHVSKEEQYYDY |
| $TT_{73-99}$ Th | 43 | YDPNYLRTDSDKDRFLQTMVKLFNRIK |
| $PT_{18-41}$ Th | 44 | GAYARCPNGTRALTVAELRGNAEL |
| $HBs_{19-32}$ Th | 8 | FFLLTRILTIPQSLD |
| $HBc_{120-140}$ Th | 45 | VSFGVWIRTPPAYRPPNAPIL |
| $HBc_{21-40}$ Th | 46 | SDFFPSVRDLLDTASALYRE |

TABLE 8-continued

AMINO ACID SEQUENCES OF FOREIGN PATHOGEN-DERIVED TH EPITOPES

| Description of Th | SEQ ID NO: | Amino Acid Sequences |
|---|---|---|
| $HB_{c50-69}$ | 47 | PHHTALRQAILCWGELMTLA |
| $TT_{615-631}$ Th | 48 | WVRDIIDDFTNESSQKT |
| HIV gp41 $Th_6$(N—) | 49 | RAGRAILHIPTRIRQGLER |
| HIV gp41 $Th_6$(C—) | 50 | AVAEGTDRVIEVLQRAGRAIL |
| CT $A8_{106-130}$ Th | 51 | ALNIWDRFDVFTLGATSGYLKGNS |
| CT $P_{11}$ Th | 13 | TINKPKGYVGKE |
| $DT_1$ Th | 52 | DSETADNLEKTVAALSILPGHG |
| $DT_4$ Th | 53 | EEIVAQSIALSSLMVAQAIPLVGELVDIGFAATNFVESC |
| PF Th | 54 | DIEKKIAKMEKASSVFNVVNS |
| SM Th | 55 | KWFKTNAPNGVDEKIRI |
| $TraT_1$ Th | 56 | GLQGKIADAVKAKG |
| $TraT_4$ Th | 57 | GLAAGLVGMAADAMVEDVN |
| $TraT_6$ Th | 58 | STETGNQHHYQTRVVSNANK |

TABLE 9

Amino Acid Sequences of Artificial Th Epitopes

| Description of Th | SEQ ID NO: | Amino Acid Sequence |
|---|---|---|
| 1,4,9 PALINDROMIC | 6 | ISEIKGVIVHKIEGI<br>  MT   RT    TRM TM<br>  L           L  V |
| Syn Th (1,2,4) | 12 | KKKIITITRIITIITTID |
| IS(1,4,9 PALINDROMIC)LF simplified | 36 | ISISEIKGVIVHKIEGILF<br>    T   RT    TR   T |
| IS(1,4,9 PALINDROMIC)LF | 59 | ISISEIKGVIVHKIEGILF<br>    MT   RT    TRM TM<br>    L           L  V |

---

I claim:

1. A CD4-CDR2 antigen peptide, wherein said antigen peptide is between about 30 and about 46 amino acids in length; wherein said CD4-CDR2 antigen peptide contains two cysteine residues separated by an intervening sequence of 28 to 40 amino acid residues; and wherein said intervening sequence is a contiguous portion of the sequence represented by residues 27 to 66 of SEQ ID NO:1, or is an immunologically functional homologue of residues 27 to 66 of SEQ ID NO:1.

2. The CD4-CDR2 antigen peptide of claim 1, wherein the antigen peptide is selected from the group consisting of SEQ ID NO:4, SEQ ID NO:5, SEQ ID NO:10, SEQ ID NO:11, and immunologically functional homologues thereof.

3. A synthetic peptide of about 50 to about 80 amino acids in length, which comprises (a) a helper T cell (Th) epitope, (b) a CD4-CDR2 antigen peptide according to claim 1; and (c) an immunostimulatory invasin domain.

4. A synthetic peptide of about 50 to about 80 amino acids in length, which comprises (a) a helper T cell (Th) epitope, (b) a CD4-CDR2 antigen peptide according to claim 2; and (c) an immunostimulatory invasin domain.

5. A peptide or peptide conjugate comprising a helper T cell epitope (Th) covalently attached to a CD4-CDR2 antigen peptide according to claim 1.

6. A peptide or peptide conjugate comprising a helper T cell epitope (Th) covalently attached to a CD4-CDR2 antigen peptide according to claim 2.

7. A peptide or peptide conjugate represented by the formula (A)$_n$-(CD4-CDR2 antigen peptide)-(B)$_o$-(Th)$_m$-X or (A)$_n$-(Th)$_m$-(B)$_o$-(CD4-CDR2 antigen peptide)-X wherein
 each A is independently an amino acid or a general immunostimulatory sequence;
 each B is selected from the group consisting of amino acids, peptide or peptide conjugate is between about 0.5 µg and about 1 mg per kilogram body weight per dose.

22. A method for inducing antibodies to surface CD4 complex in a mammal which comprises administering to said mammal a pharmaceutical composition according to claim 20.

23. A method for inducing antibodies to surface CD4 complex in a mammal which comprises administering to said mammal a pharmaceutical composition according to claim 21.

* * * * *